US009803200B2

(12) United States Patent
Henshall et al.

(10) Patent No.: US 9,803,200 B2
(45) Date of Patent: Oct. 31, 2017

(54) INHIBITION OF MICRORNA-134 FOR THE TREATMENT OF SEIZURE-RELATED DISORDERS AND NEUROLOGIC INJURIES

(71) Applicant: ROYAL COLLEGE OF SURGEONS IN IRELAND, Dublin (IE)

(72) Inventors: David Henshall, Dublin (IE); Eva Jimenez-Mateos, Dublin (IE)

(73) Assignee: Royal College of Surgeons in Ireland, Dublin (IE)

( * ) Notice: Subject to any disclaimer, the term of this patent is extended or adjusted under 35 U.S.C. 154(b) by 0 days.

(21) Appl. No.: 15/002,107

(22) Filed: Jan. 20, 2016

(65) Prior Publication Data
US 2016/0369270 A1    Dec. 22, 2016

Related U.S. Application Data

(63) Continuation of application No. 14/348,396, filed as application No. PCT/EP2012/069251 on Sep. 28, 2012, now abandoned.

(60) Provisional application No. 61/540,477, filed on Sep. 28, 2011.

(51) Int. Cl.
| | |
|---|---|
| *C12N 15/11* | (2006.01) |
| *C12N 15/113* | (2010.01) |
| *A61K 48/00* | (2006.01) |
| *C07H 21/04* | (2006.01) |

(52) U.S. Cl.
CPC ...... *C12N 15/113* (2013.01); *C12N 2310/113* (2013.01); *C12N 2320/32* (2013.01)

(58) Field of Classification Search
None
See application file for complete search history.

(56) References Cited

U.S. PATENT DOCUMENTS

2010/0317715 A1*  12/2010  Vollrath ............. A61K 31/4365
                                                    514/44 A

FOREIGN PATENT DOCUMENTS

| WO | 2005/013901 A2 | 2/2005 |
|---|---|---|
| WO | 2007/044937 A2 | 4/2007 |

OTHER PUBLICATIONS

Gao et al., "A novel pathway regulates memory and plasticity via SIRT1 and miR-134", Nature, vol. 466, No. 7310, pp. 1105-1109, 2010.
Jimenez-Mateos et al., "Silencing microRNA-134 produces neuroprotective and prolonged seizure-suppressive effects", Nature Medicine, vol. 18, No. 7, pp. 1087-1094, 2012.
Schratt et al., "A brain-specific microRNA regulates dendritic spine development", Nature, vol. 439, No. 7074, pp. 283-289, 2006.
Shetty, "Promise of resveratrol for easing status epilepticus and epilepsy", Pharmacology and Therapeutics, vol. 131, No. 3, pp. 269-286, 2011.
Walter et al., "Insights into brain development from neurogenetic syndromes: evidence from fragile X syndrome, Williams syndrome, Turner syndrome and velocardiofacial syndrome", Neuroscience, vol. 164, No. 1, pp. 257-271, 2009.
Christensen et al., "Recombinant adeno-associated virus-mediated microRNA delivery into the postnatal mouse brain reveals a role for miR-134 in dendritogenesis in vivo", Frontiers in Neural Circuits, vol. 3, Article 16 (2010).
Jimenez-Mateos et al., "Silencing microRNA reduces seizures, hippocampal injury and epileptogenesis", The 6th Annual Meeting of Neuroscience Ireland, Sep. 1 and 2, 2011.
Pitkanen et al., "Mechanisms of epileptogenesis and potential treatment targets", Lancet Neurol, 10:173-86 (2011).
Krutzfeldt et al., "Silencing of microRNA in vivo with antagomirs", Nature, 438-685-689 (2005).

* cited by examiner

*Primary Examiner* — Dana Shin
(74) *Attorney, Agent, or Firm* — Nixon Peabody LLP; David S. Resnick; Nicole D. Kling

(57) ABSTRACT

A method for preventing or treating epilepsy or status epilepticus, or a brain-related disorder which is characterized by precipitation of seizures, in an individual. The method comprises the step of treating the individual with an agent that inhibits the activity of miR-134 in the individual. The agent is delivered to the brain of the individual.

15 Claims, 13 Drawing Sheets

INHIBITION OF MICRORNA-134 FOR THE TREATMENT OF SEIZURE-RELATED DISORDERS AND NEUROLOGIC INJURIES

CROSS-REFERENCE TO RELATED APPLICATIONS

This Application is a continuation of U.S. Ser. No. 14/348,396 filed on Mar. 28, 2014, which is a 35 U.S.C. §371 National Phase Entry Application of International Application No. PCT/EP2012/069251 filed Sep. 28, 2012, which designates the U.S., and which claims benefit under 35 U.S.C. §119(e) of U.S. Provisional Application No. 61/540,477, filed on Sep. 28, 2011, the contents of each of which are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 26, 2014 is named 10749PC00_ST25.txt and is 3308 bytes in size.

FIELD OF THE INVENTION

The invention relates to a drug/therapeutic strategy to treat or prevent the development of seizure-related disorders and neurologic injuries. In particular, the invention relates to inhibiting mircoRNA-134 in the brain of mammals to treat or prevent the development of seizure-related disorders and neurologic injuries.

BACKGROUND TO THE INVENTION

Epilepsy is a serious, chronic neurologic disorder characterised by recurrent spontaneous seizures which affects about 50 million people worldwide and the socioeconomic cost in Europe of epilepsy is thought to be 15.5 billion euro per year (with a similar cost estimate in the U.S.A.). And epileptic drugs typically control seizures in two-thirds of patients but probably do not alter the underlying pathophysiology. The remaining one-third of people with epilepsy are either drug-resistant or suffer unacceptable side effects from available drugs and continue to have seizures, leaving patients with few options, for example, brain surgery to remove part of the brain causing the seizures. The development of symptomatic (acquired) epilepsy is thought to involve altered expression of ion channels and neurotransmitter receptors, synaptic remodelling, inflammation, gliosis and neuronal death, among others. However, few anti-epileptogenic interventions targeting the processes have shown sufficient efficacy in vivo, and our understanding of the cell and molecular mechanisms remains incomplete. There is currently no prophylactic treatment ("anti-epileptogenic") following a brain injury likely to precipitate epilepsy. Similarly, there is no specific neuroprotective treatment for status epilepticus (SE), or treating acute neurolgic injuries likely to cause brain damage or epilepsy, for example, stroke, trauma.

Evidence is emerging that microRNAs (miRNAs) may be critical to the pathogenesis of several neurologic disorders, including epilepsy. miRNAs are a family of small (~22 nt), endogenously expressed non-coding RNAs which regulate mRNA translation by imperfect base-pairing interactions within the 3' untranslated region. Depending on the degree of sequence complementarity, miRNA binding, which occurs via Argonaute proteins within the RNA-induced silencing complex (RISC), results in either cleavage or a reduction in the translational efficiency of the target mRNA.

miR-134 is a brain-specific, activity-regulated miRNA implicated in the control of neuronal microstructure. Pyramidal cells are the most common neuron in the neocortex and hippocampal formation. They are the major source of intrinsic excitatory cortical synapses, and their dendritic spines are the main postsynaptic target of excitatory synapse, with spine size and index of synaptic strength. In the adult brain, spines are quite stable but remodelling occurs during learning and memory formation, as well in the setting of neuropsychiatric disorders and pathological brain activity. Spine collapse is mediated in part by N-methdyl-D-aspartate (NMDA) receptor/calcium-dependent de-polymerisation of actin by cofilin. LIM kinase-1 (Limk1) phosphorylates and inactivates cofilin and loss of Limk1 results in abnormal spine morphology. In hippocampal neurons, miR-134 targets Limk1 mRNA, thereby preventing Limk1 protein translation. Over-expression of miR-134 in vitro has been reported to reduce spine volume, whereas over-expression of miR-134 in vivo using viral vectors reduces total dendritic length and abrogates long-term potentiation (LTP). Mice lacking the miRNA biogenesis component Dgrc8 fail to produce several mature miRNA s, including miR-134, and display reduced hippocampal spine density. Spine loss may have divergent functional consequences according to context, promoting excitability or uncoupling NMDA receptor-driven currents in neurons and preventing excitotoxicity.

There is therefore a need to provide a treatment or preventative measure that specifically targets the process by which epilepsy and other neurological injuries likely to cause brain damage develop and that overcome some of the above-mentioned problems.

SUMMARY OF THE INVENTION

According to the present invention there is provided, as set out in the appended claims, a method of preventing or treating epilepsy or status epilepticus, or preventing development or occurrence of seizures in an individual suffering from a brain-related pathology characterised by development of seizures, or treating acute neurological injuries that are likely to cause brain damage or precipitate epilepsy or seizures, in an individual in need thereof, the method comprising a step of inhibiting miR-134 activity in the individual. Suitably, the method involves treating the individual with a therapeutically effective amount of an agent capable of inhibiting miR-134 activity, for example a miR-134 antagomir, in which the agent is typically delivered to the brain of the individual.

The Applicants have shown, as set out in the appended Figures, in vivo blocking of miR-134 in brain results in significant reduction of spine density (FIG. 3d-f), strongly inhibits seizures occurring (FIG. 4), pin-pointed Lim kinase-1 as being important for the neuroprotective effect of miR-134 in a well-established model of excitotoxicity (FIG. 5g-i) (the core pathophysiologic component of stroke) and potently limits the development of epilepsy (FIG. 6a-f). Furthermore, the Applicants have also shown that the gene for miR-134 is over-produced in the brains of mice and humans with epilepsy (FIG. 1). Antagomirs against miR-134 can be delivered intra-nasally to reduce brain-levels of miR-134 and affect seizures (FIG. 10).

In one embodiment of the present invention there is provided an agent capable of inhibiting the activity of miR-134 for use in preventing or treating epilepsy or status epilepticus in an individual, wherein the agent is delivered to the brain of the individual.

In a further embodiment of the present invention, there is provided an agent capable of inhibiting the activity of miR-134 for use in preventing the development or occurrence of seizures in an individual having a brain-related disorder characterised by development of seizures, wherein the agent is delivered to the brain of the individual.

In one embodiment of the present invention, the brain-related disorder characterised by development of seizures is selected from the group consisting of stroke, hypoxia, traumatic brain injury, infection, tumor, neurodegenerative disorders, metabolic and autoimmune disorders causing seizures.

In a further embodiment of the present invention, there is provided an agent capable of inhibiting the activity of miR-134 for use in preventing the development of epilepsy or occurrence of seizures in an individual that has suffered a brain injury likely to precipitate epilepsy or seizures, or cause or have caused brain damage.

In a further embodiment of the present invention, there is provided an agent capable of inhibiting the activity of miR-134 for use in treating or preventing refractory epilepsy.

In a further embodiment of the present invention, there is provided an agent capable of inhibiting the activity of miR-134 for use in treating or preventing brain damage in an individual that has suffered a brain injury likely to cause or have caused brain damage, for example individuals that have suffered acute neurological injuries such as stroke or brain trauma.

In one embodiment of the present invention, the agent capable of inhibiting miR-134 does so by inhibiting miR-134 expression and/or inhibiting miR-134 activity.

In one embodiment of the present invention, miR-134 activity is inhibited by means of a miR-134 antagomir.

In one embodiment of the present invention, the antagomir has a sequence selected from SEQ ID NO: 5, or functional variants thereof.

In one embodiment of the present invention, the agent inhibiting miR-134 is selected from the group comprising: antagomirs, microRNA sponges, tiny seed-targeting LNA oligonucleotides, anti sense oligonucleotides, short-interfering RNA, decoy oligonucleotides, aptamers, and antibodies that specifically recognize DNA:RNA heteroduplexes.

In a further embodiment of the present invention, there is provided, a method of identifying compounds useful in the treatment or prevention of a pathology characterised by seizures, comprising contacting human miR-134 RNA with a candidate compound, and determining the level of activity of the contacted miR-134 RNA, wherein a decrease in the level of activity of the contacted miR-134 RNA relative to a reference level of activity of human miR-134 that is not contacted with the compound is an indication that the candidate compound is useful in the treatment or prevention of a pathology characterised by seizures. Typically, the miR-134 RNA is from a human.

In one embodiment of the present invention, the miR-134 RNA is provided in the form of miR-134 expressing cells, and in which the level of activity is determined by assaying for a level of expression of miR-134 RNA in the cells.

In one embodiment of the present invention, the pathology characterised by seizures is selected from the group comprising, epilepsy, status epilepticus, stroke, hypoxia, traumatic brain injury, infection, tumor, neurodegenerative disorders, metabolic and autoimmune disorders causing seizures.

In a further embodiment of the present invention, there is provided a use of an agent capable of inhibiting the expression or activity of miR-134 as a medicament.

In a further embodiment of the present invention, there is provided a pharmaceutical composition for use in treating or preventing a neuronal pathology characterised by seizures, for example stroke or brain trauma, the composition comprising an agent capable of inhibiting the activity of miR-134 in combination with a pharmaceutically acceptable excipient.

In one embodiment of the present invention, the agent inhibiting the activity of miR-134 is a miR-134 antagomir, microRNA sponges, tiny seed-targeting LNA oligonucleotides, antisense oligonucleotides, short-interfering RNA, decoy oligonucleotides, aptamers, and antibodies that specifically recognize DNA:RNA heteroduplexes.

In a further embodiment of the present invention, there is provided an agent capable of inhibiting the activity of miR-134 for use in preventing spontaneous recurrent seizures in an individual, wherein the agent is delivered to the brain of the individual.

In a further embodiment of the present invention, there is provided an agent capable of inhibiting the activity of miR-134 for use as an anti-epileptogenic agent in an individual having a brain injury likely to precipitate epilepsy.

The invention also provides methods of screening for compounds useful in treating pathologies characterised by seizures. Diseases or conditions associated with this pathology will be well known to those skilled in the art. Typically, the disease or condition is selected from the group comprising: epilepsy syndromes (a collective term for ~40 clinically distinct syndromes all characterized by an enduring predisposition to recurrent unprovoked seizures), and status epilepticus (SE; a single continuous seizure lasting 30 min or more, or a continuous series of seizures without recovery of consciousness between them. Shorter operational definitions are in common use, such as a single seizure lasting more than 5 minutes). Other conditions include those associated with the development of seizures, for example stroke, hypoxia, traumatic brain injury, neurodegenerative diseases, metabolic disorders and autoimmune disorders. Thus, the invention also provides for preventing the occurrence or development of seizures in an individual suffering from a disease or condition which is characterised by development of seizures.

The invention also relates to a pharmaceutical composition comprising an agent capable of inhibiting miR-134 activity in an individual in combination with a pharmaceutically acceptable carrier. The inhibitor is typically selected from in antagomir of miR-134.

In another aspect, the invention relates to the use of miR-134 levels in an individual, typically levels of miR-134 in the brain or neuronal tissue of an individual, as a diagnostic or prognostic variable of epilepsy or status epilepticus, or as a means of predicting the occurrence or development of seizures in an individual suffering from a condition or disease which is known to lead to seizures, for example stroke or infection. Generally, an increased level of miR-134 compared to a control correlates with a positive diagnosis or prognosis, in which the control is suitably the level of miR-134 in an individual not suffering from epilepsy or status epilepticus, or in the case of prediction of seizure, the control may be the level of miR-134 from an individual suffering from the condition or disease and in which seizures did not occur or develop (for example, an individual who suffered a stroke but did not develop seizures as a result of the stroke).

Preferably, the agent capable of inhibiting the activity miR-134 is an antagomir. Examples of suitable antagomirs are provided below.

BRIEF DESCRIPTION OF THE DRAWINGS

The invention will be more clearly understood from the following description of an embodiment thereof, given by way of example only, with reference to the accompanying drawings, in which:

FIG. 1A depicts Representative photomicrographs (24 hr) showing neuronal death (FJB) in CA3 stratum pyramidale (s.p.) after SE but not in a vehicle-injected control (Cont). Panel below shows representative EEG trace and frequency/amplitude heat map of seizures during SE. FIG. 1B depicts In situ hybridisation localising miR-134 mainly to cell bodies of CA3 pyramidal neurons. FIG. 1C depicts Real-time qPCR (RT-qPCR) measurement of miR-134 expression normalized to RNL19 for CA3 (P=0.016) and CA1 (P=0.035) 24 hr after SE. *P<0.05 compared to Cont; n=5 per group. FIG. 1D depicts RT-qPCR analysis of Ago-2-eluted miR-134 in Cont and SE mice at 24 hr, *P<0.01 compared to Cont (n=5 per group). FIG. 1E is a graph and immunoblot showing expression of Limk1 in hippocampus samples from mice 24 h following status epilepticus (SE) compared to control (Cont.) FIG. 1F depicts Photomicrographs showing typical CA3 subfield damage (loss of neurons (NeuN—arrows) and astrogliosis (GFAP, green)) in epileptic mice 14 days after SE. FIG. 1G depicts RT-qPCR analysis of miR-134 in epileptic mice for CA3 (P=0.806 for 1 week (1 w) and P=0.049 for 3 w) and CA1 (1 w, P=0.003; 3 w, P=0.08). 8P<0.05 compared to Cont; n=5 per group. FIG. 1H depicts Limk1 in Cont and epileptic mice at 1 w and 3 w. Actin is included as a guide of protein loading. Graph summarises densitometry data (*P=0.028; n=4 per group). FIG. 1I depicts Graph and blot (n=1 per lane) showing expression of miR-134 and Limk1 in temporal lobe samples from patients with pharmacoresistant epilepsy (TLE) compared to autopsy controls (Cont) (*P=0.029; n=3 per group). Densitometry analysis of Limk1 levels showed levels were lower in TLE tha Cont (Unpaired t-test, P-0.039, n=3 per group, not shown). Scale bars: a-b, f 200 μm.

FIG. 7A depicts the primary sequence of miR-134 during DICER processing of SEQ ID NO: 2; sequence of the mature form of miR-134 (SEQ ID NO:1) and sequence of the antagomir targeting miR-134 (SEQ ID NO:5). FIG. 7B depicts RT-qPCR showing levels of miR-134 after injection of 0.5 nmol and 1.0 nmol of either Scr or Ant-134 (ANOVA, *p<0.05 compared to aCSF, #p<0.05 compared to Scr). FIG. 7C depicts (e) qPCR showing levels of an unrelated microRNA (miR-19a) at 0.5 nmol and 1.0 nmol of scramble and antagomir-134 (ANOVA, *p<0.05 compared to aCSF).

FIG. 8 shows representative frequency-amplitude EEG heatmaps from two animals given Loraz followed by KA with recordings continued for 40 min, as before. The extent of seizure suppression was qualitatively similar to that seen with pre-treatment with Ant-134 (see FIG. 4c).

DETAILED DESCRIPTION OF THE DRAWINGS

Figure 1:
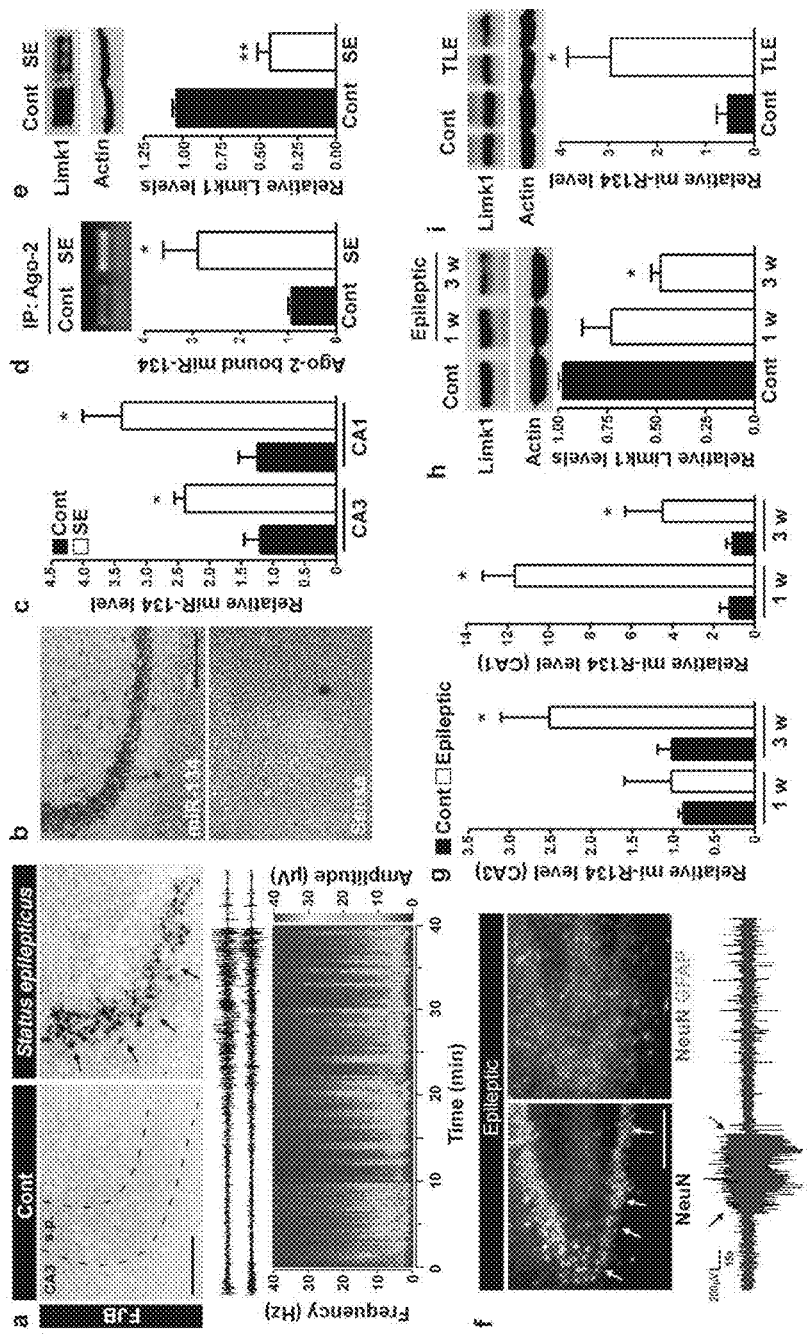
FIGS. 1A-1I illustrate miR-134 changes following status epilepticus (SE) and in epilepsy.

Definitions microRNA's (miRNAs) are small (~22 nt) non-coding RNAs (ncRNAs) that regulate gene expression at the level of translation. Each miRNA apparently regulates multiple genes and hundreds of miRNA genes are predicted to be present in mammals. Recently miRNAs have been found to be critical for development, cell proliferation and cell development, apoptosis and fat metabolism, and cell differentiation.

In the specification, the term "miR-134" should be understood to mean a brain-specific, activity-regulated miRNA implicated in the control of neuronal microstructure. Pyramidal cells are the most common neuron in the neocortex and hippocampal formation. They are the major source of intrinsic excitatory cortical synapses, and their dendritic spines are the main postsynaptic target of excitatory synapse, with spine size and index of synaptic strength. In the adult brain, spines are quite stable but remodelling occurs during learning and memory formation, as well in the setting of neuropsychiatric disorders and pathological brain activity. Over-expression of miR-134 in vitro has been reported to reduce spine volume, whereas over-expression of miR-134 in vivo using viral vectors reduces total dendritic length and abrogates long-term potentiation (LTP). Mature human miR-134 has a sequence UGUGACUGGUUGACCA-GAGGGG (SEQ ID NO: 1). The primary sequence of human miR-134 is provided below:

```
                                               (SEQ ID NO: 2)
GGACCACAATTTCAACTCCAGGGAAGGGGGACTGTGCCAGCACCACTCCA

AGGGAGGTGAGTGAAGGGTTGCCCAAACTCCAGTGTGTTCCTAGGACACC

CGTAAGCTGCCTCACTAATGCTCGGTGTCCACTCTGTCCACAGGATGGTG
```

-continued

```
GTTGGCAGCCACTCCCCTTGGAGAAGTGGAAGGGGACTCCTTGTCTGTCT

TGTCTCTGCTTTTCTGTGGTACTTGAAGAGAAGTTGTTCGTGGTGGATTC

GCTTTACTTATGACGAATCATTCACGGACAACACTTTTTTCAGTACCAAA

TGCTACCTCTAAGGACTTCCTGGACACAATGGCAGCTTCAGGAAAGATAG

TCTTTGTGTCAACCATGTGGAAAAGCCAAGAATGGATGGCGGGCCATGGA

CAATGCGCTGACCTAGCTGTAAGTCACCTGGCCCGATAATCCGAGCCTCC

CATGCACCTATAGGAGGTCTTCCCATGGGTCTCACCAACTCTGGGGAATC

AGCTGTGGTTCTGTCACCAGCGTCACCTCACAAGACTTTGAAGAGAGGCT

CCCTGGGCCCCAGGCCGACTTCCAGAAGAGATGTTGGTGTCAGCACCCTT

CCAGGGTGTGTGACTGGTTGACCAGAGGGGCATGCACTGTGTTCACCCTG

TGGGCCACCTAGTCACCAACCCTCAGCATCACTCCCACTCCAGGAAGACT

TTCCAGAGCTCCCACCAACTCTGGGGAAGCGGCCATGGACTTGCTCGTGA

CTGCTTGGTGGACTGCCATGACACCTTGCTCTTGGGGGTGTATGTTTACT

TAAAATGCAATGAGTCAGCCTTGGCAGCCCCTTCACCACTGTGACAGCCT

CCTTGAAGTGTTGACTTCCGATGTGGGACGCCATGTTGTCTTCTGTTGAG

GGACCTCGATGTGGGCCAGCTTTTCTCCTGGGTGTGTGACTGAATCCTTC

TTCCCAGACTCATGTGCTGCCTTTGTTAGGTCTGTCACGTCGTCCTCTAA

TACCCAGCATCCTGTCTCTCCCTAGGAGGCTCCATGGAGATAATGCGGCT

TTGGGAAGCGGCCATGATTCTCCTGTCAGGGACCAGTGAGCTACGCAAAA

GCTCCCTGTCTTGTCTGGAAGGACGAACTGCATCCTTGCTGCTGGGGAGA

AGGCAGTGCCCTCAGCACTCCCTTAAGGTAAGTGCGCCTCGGGTGAGCAT

GCACTTAATGTGCTGTGTATGTCACTCGGCTCGGCCCACTACCCAATACT

ATCCCACCCATTCCTAACAGGACTCCCGA.
```

The precursor sequence of human miR-134 is highlighted in hold above and is as defined in SEQ ID NO: 3:

```
CAGGGTGTGTGACTGGTTGACCAGAGGGGCATGCACTGTGTTCACCCTGT
GGGCCACCTAGTCACCAACCCTC.
```

The term "human miR-134" should also be taken to include any human miR-134 paralogues.

In the specification, the term "inhibition of miR-134 activity" should be understood to mean preventing miR-134 carrying, out its function(s) typically including controlling neuronal microstructure. Generally, inhibiting miR-134 activity should be understood to include direct inhibition in which a molecule binds to miR-134 and directly inhibits its activity (for example, a low molecular weight inhibitor or a binding partner such as an antibody or antibody fragment) and indirect inhibition in which, for example, expression of the miRNA molecule is modulated by suitable means including for example use of repressors or small interfering RNA molecules. Inhibition of miR-134 function should be understood to encompass administering any molecule which directly or indirectly inhibits the mature form of miR-134 (SEQ ID NO: 1), as well as molecules which target the precursor form of miR-134 (SEQ ID NO: 3), primary miR-134 (SEQ ID NO: 2), or any human miR-134 paralogues. The term should also include administering molecules which interfere with miR-134 function by enhancing expression of its target mRNA transcripts, including but not limited to Limk1, and molecules which target the biogenesis of miR-134 and might thereby be capable of inhibiting production of miR-134 such as molecules targeting the transcription regulation of SEQ ID NO: 2 or other steps in miR-134 biogenesis (for instance, molecules that inhibit Argonaute-2, Drosha/DGCR8 or Dicer). The antisense targeting region of miR-134 is defined by SEQ ID NO: 6: UCUCUCCCUCUGGUCAACCAGUCACAAGGCU.

Thus, the agent capable of inhibiting miR-134 activity may be a molecule capable of specifically binding to the antisense targeting region of miR-134 shown is SEQ ID NO: 6. An example of such an agent is a reverse complementarity sequence (e.g. as an oligo or antisense nucleotide) as shown in SEQ ID NO 7: CCCCTCTGGTCAACCAGTCACA.

In the specification, the term "agent capable of inhibiting miR-134 activity" should be understood to mean any agent which may inhibit, ideally specifically inhibit, the expression of or activity miR-134. Suitable agents include antagomirs, antisense molecules, small hairpin RNA molecules, small interfering RNA molecules, microRNA sponges, tiny seed-targeting locked nucleic acid (LNA) oligonucleotides, decoy oligonucleotides, aptamers, ribozymes, or antibodies that specifically recognize DNA:RNA heteroduplexes. Small hairpin RNA (shRNA) molecules are short RNA molecules having a small hairpin loop in their tertiary structure that may be employed to silence genes. The design of shRNA molecules capable of inhibiting miR-134 will be apparent to those skilled in the field of shRNA molecule design. As an alternative, the level of miR-134 expression can be modulated using antisense or ribozyme approaches to inhibit or prevent miR-134 activity, or triple helix approaches to inhibit transcription of miR-134.

In the specification, the term "brain-related disorder characterised by development of seizures" should be understood to mean a brain injury or condition that can precipitate seizures or epilepsy, such as for example, stroke, CNS infection-associated seizures, brain tumors, traumatic brain injury, neurodegenerative disorders, metabolic disorders causing seizures (including but not limited to hypoglycaemia, glycogen storage diseases, pyruvate dehydrogenase deficiency, acquired hypoparathyroidism. Adeuylosuceinate lyase (ADSL) deficiency) and autoimmune disorders causing seizures (multiple sclerosis, diabetes melitus and systemic lupus erythematosus). Thus, while the invention relates to preventing the development of seizures in individuals suffering from such disorders or conditions, the invention does not provide a treatment for the underlying condition (i.e. stroke).

The term "brain injury likely to precipitate epilepsy or seizures, or cause or have caused brain damage" should be understood to mean stroke, trauma or other types of acute neurological injuries.

In the specification, the term "antagomir" should be understood to mean a novel class of chemically engineered oligonucleotides. Antagomirs are used to silence endogenous microRNA. An antagomir is a small synthetic oligonucleotide that is complementary to the specific miRNA target with either mispairing at the cleavage site of Arganoute 2 (Ago2) or some sort of base modification to inhibit Ago2 cleavage. Usually, antagomirs have some sort of modification, such as 2 methoxy groups, 3'-cholesterol groups, phosphorothioates, to make it more resistant to degradation. It is believed that antagomirs inhibit by irreversibly binding the miRNA. An example of antagomirs suitable for use in inhibiting the activity of miR-134 are molecules comprising the oligonucleotides CCTCTGGTCAACCAGTCAC (SEQ ID NO: 5), or variants thereof that have at least 80%, 85%, 90%, 95% or 99% sequence identity with SEQ ID NO: 5 when determined using the sequence alignment program BLAST, and which are capable of silencing human miR-134. Ideally, the antagomir molecule comprises a base modification to make it more resistance to degradation, for example a 2' methoxy group, 3'-cholesterol group, or phosphorothioate, modification.

In this specification, the term "biological system" should be taken to include a cell, a cell line, a tissue sample, an organ, a unicellular or multicellular organism, or a lower or higher life form.

Figure 9:
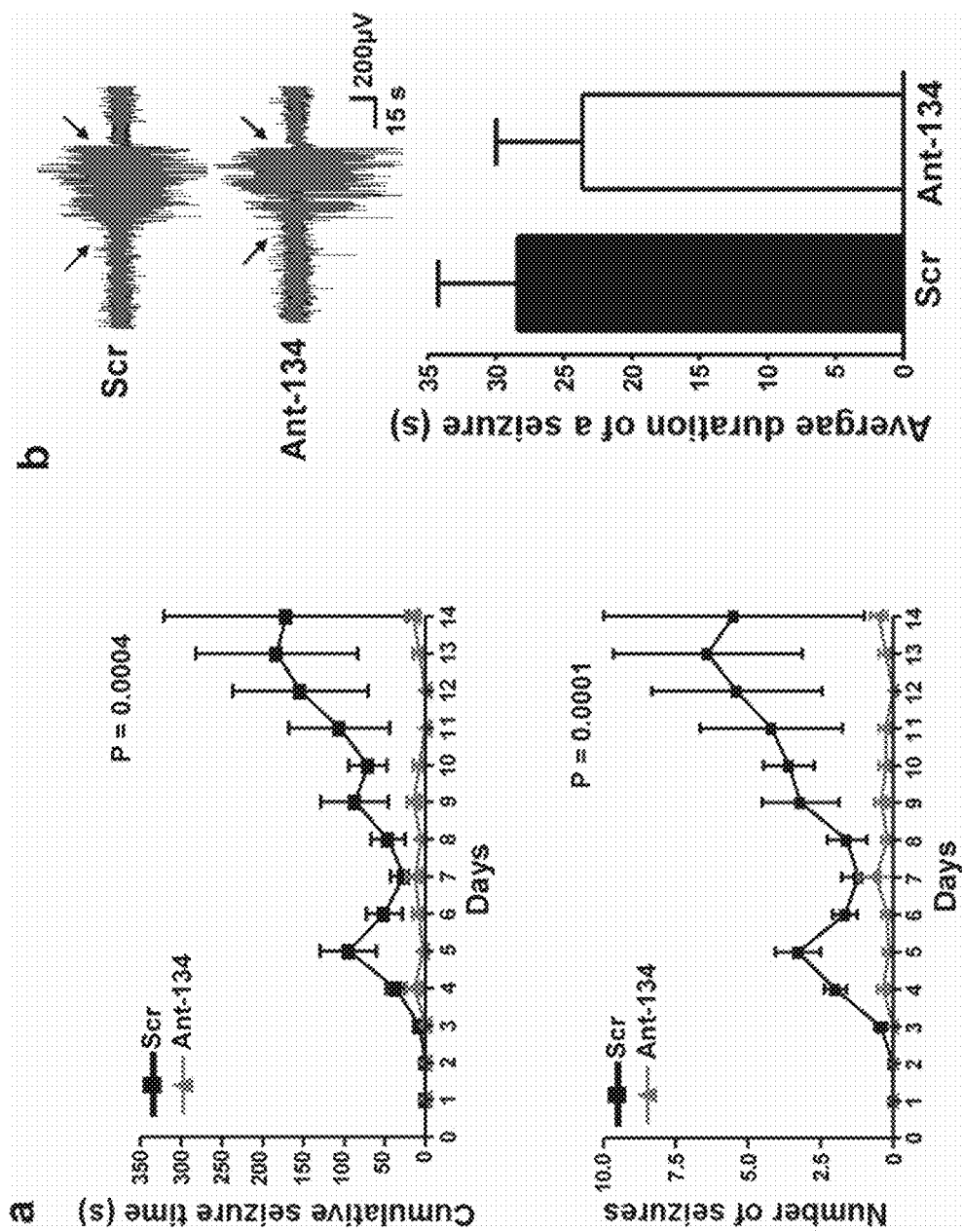
FIG. 9 Effects of Ant-134 on epileptic seizures. (a) Graphs showing cumulative time in seizures per day and mean number of epileptic seizures per day for Scr and Ant-134 animals. Two-way ANOVA confirmed groups were statistically different. (b) Representative EEG traces of typical spontaneous seizures captured using EEG telemetry. Graph below shows the duration of an individual seizure, when they occurred, was not different between groups (P=0.610, n=5 per group).
Figure 10:
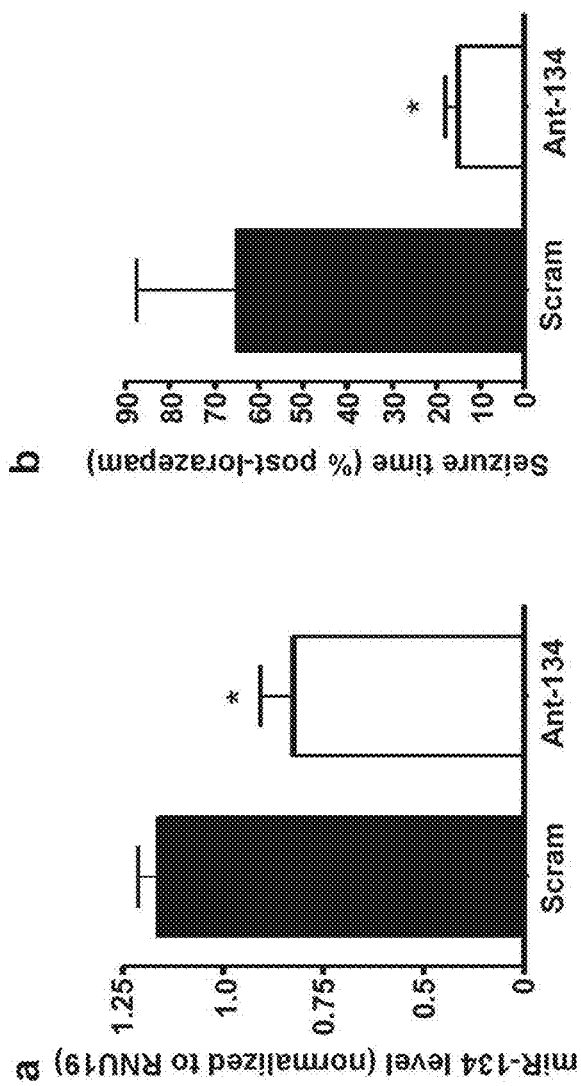
FIG. 10 Effect of intra-nasal antagomirs targeting miR-134. Antagomirs or scrambled were applied to the nostril of mice (5 µL/0.3 nmol) and hippocampal levels of miR-134 measured 24 h later. Ant-134 reduced hippocampal levels when given intranasally, albeit to a lesser extent than when given i.c.v. A group of mice were then subjected to status epilepticus and seizure durations were measured. Mice given Ant-134 experienced reduced seizures post-lorazepam administration (*P=0.05), although seizure duration between KA injection and lorazepam was not different, likely because the reduction in miR-134 levels achieved using this particular dose of Ant-134 only reduced miR-134 levels by ~40%).

Various delivery systems are known and can be used to administer a therapeutic of the invention, e.g., intra-nasally (see FIG. 9). Methods of introduction include but are not limited to intradermal, intramuscular, intraperitoneal, intravenous, subcutaneous, intranasal, epidural, intranasal, intracerebral, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

Preferably, the therapeutic is delivered to the CNS or PNS. Delivery means include intravenous delivery, oral delivery, intramuscular delivery, intrathecal delivery, and inhaled delivery. Methods for achieving these means of delivery will be well known to those skilled in the art of drug delivery, and include:

- Delivered intrathecally by mini-osmotic pump, (ref: Ignacio et al., Ann, N.Y. Acad. Sci. 2005, 1053: 121-136),
- Intramuscular delivery directly into muscle(s) by syringe or mini osmotic pump (Azzouz et al., Nat Med. 2005; 11(4):429-33).
- Intraperitoneal—for systemic administration—directly administered to peritoneum by syringe or mini osmotic pump (Kieran et al., Nat Med 2004; 10(4):402).
- Subcutaneous—for systemic administration—directly administered below the skin by syringe (Reinholz et al., Exp Neurol. 1999; 159(1):204-16).
- Intraventricular—direct administration to the ventricles in the brain, by injection or using small catheter attached to an osmotic pump. (Sathasivam et al., 2005 Neuropath App Neurobiol; 31(5): 467)
- Implant—can be prepared in an implant (eg small silicon implant) that will release Active. Implant can be placed at muscles or directly onto the spinal cord (Kieran and Greensmith, 2004 Neurosci 125(2):427-39).

It may be desirable to administer the compositions of the invention locally to the area in need of treatment; this may be achieved, for example and not by way of limitation, by topical application, by injection, by means of a catheter by means of a suppository or by means of an implant, said implant being of a porous, non-porous, or gelatinous material, including membranes, such as sialastic membranes, or fibers.

The present invention also provides pharmaceutical compositions. Such compositions comprise a therapeutically effective amount of the therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. In this specification, the term "therapeutically effective amount" should be taken to mean an amount of therapeutic which results in a clinically significant inhibition, amelioration or reversal of development or occurrence of seizures or, in the case of treatment of stroke, clinically significant inhibition, amelioration or reversal of development of the effects of stroke.

The term "carrier" refers to a diluent, adjuvant excipient or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Materials Methods

Seizure Models.

Adult male C57BL/6 mice (Harlan) were used in all studies. SE was induced by intra-amygdala KA, with seizures terminated after 40 minutes by lorazepam (6 mg/kg, i.p.). Non-harmful seizures were produced by systemic injection of 15 mg/kg KA. EEG was quantified by manual counting high amplitude high frequency discharges and using LabChart Pro v7 frequency/amplitude analysis software (ADInstruments).

Epilepsy Monitoring.

Mice were equipped with two-channel EEG telemetry units (Model:F20-EET, Data Systems International) which were fitted into a subcutaneous pocket behind the shoulder blades. EEG was analyzed using TWin® software and the duration of HAHFDs, also termed as type IV seizures, was calculated between the time of KA injection and the time of lorazepam administration by an observer blinded to treatment group. Additional frequency and amplitude analysis of EEG was performed by uploading data to an automated programme for EEG analysis (LabChart Pro v7 software, ADInstruments Ltd).

Human Samples.

Fresh frozen samples of temporal lobe neocortex were obtained from patients who underwent surgical resection for the treatment of pharmacoresistant epilepsy at Beaumont Hospital, Dublin, Ireland. Control (autopsy) tissue was obtained from the Brain and Tissue Bank for Developmental Disorders at the University of Maryland, Baltimore, Md. and was from people who died of cause unrelated to neurological disease.

Histopathology.

Cell death was assessed using Fluoro-Jade® B, terminal deoxynucleotidyl transferase dUTP nick end labeling (TUNEL) and by staining for the mature neuronal marker NeuN on coronal brain sections. Neuropepetide Y immunostaining was scored as per Jimenez-Mateos et al., Neuroscience, Vol. 171, pages 556-565 (2010).

miRNA Expression.

Total RNA was extracted from individual microdissected hippocampal subfields and reverse transcribed using stemloop Multiplex primer pools (Applied Biosystems). RT specific primers for mouse miRNAs miR-19a and miR-134 (Applied Biosystems) were used and qPCRs carried out on a 7900HT Fast Realtime System (Applied Biosystems) using Taqman microRNA assays (Applied Biosystems). RNU19 or U6B were used for normalisation.

Western Blotting.

Protein was extracted from individual microdissected CA3 subfields, subjected to SUS-PAGE, transferred to nitrocellulose membranes and visualised with primary and secondary antibodies with chemiluminescence.

In Situ Hybridisation.

Brains were perfused with 4% paraformaldehyde, sectioned and mounted and incubated with a 5'-digoxigenin-labelled,2'-O,4'-C methylene bicyclonucleoside miR-134 probe. Probe was visualised using anti-DIG and colour substrate (Roche).

Argonuate Immunoprecipitation.

Argonuate-2 was immunoprecipitated from CA3 subfields using protein-A agarose beads followed by miRNA extraction and Rt-qPCR.

Antagomirs.

Scr (SEQ ID NO: 4—CGTCTAGCCACCTAG-Chol-TEG) or Ant-134 (SEQ ID NO: 5—CCTCTGGTCAACCA-GTCAC-Chol-TEG) (Exiqon, LNA- and 3'-cholesterol modified oligonucleotides) in artificial cerebrospinal fluid (aCSF) (Harvard Apparatus) were injected into the lateral ventricle of the mouse.

Ethogram.

Exploratory activity was assessed in an open field apparatus (ENV-510) over a data collection period of 60 minutes.

Spine Density Analysis.

Pyramidal cells in the CA3 region of hippocampal slices (150 µm) were individually injected with Lucifer yellow, processed using anti-Lucifer yellow and imaged using a Zeizz (LSM 710) confocal microscope. Image stacks were analysed using Imaris 7.1 image processing software and spine density calculated for each dendrite by dividing its length by the number of spines and also analysed as a function of its distance from soma (Sholl analysis) by dividing the length of the dendritic segment by the number of spines in this distance for every 10 µm distance from the soma.

Intracerebroventricular Injections.

For i.c.v. injections, additional mice were affixed with a cannula ipsilateral to the side of KA injection. Coordinates from Bregma were: AP=−0.3 mm, L=−1.0 mm. V=−2.0 mm. Mice received 1 µL infusion of either Scr or Ant-132 LNA- and 3'-cholesterol modified oligonucleotides (Exiqon) in aCSF (Harvard Apparatus). Mice were either euthanized or underwent SE. For experiments involving intranasal administration of antagomirs, 0.12 nmol of scramble or antagomir in a 5 µl volume was administrated into each nostril of the mice. Mice were euthanized at various time points after antagomirs (1, 4, 8, 12 or 24 h, and 3, 5, 7, 14, 28 days and 2 months), after KA or vehicle (24 h), or once animals began to display spontaneous seizures at 1, 2, 4 or 8 weeks after intra-amygdala injections.

Analysis of Spontaneous Seizures Using EEG Telemetry.

Epilepsy monitoring via implanted EEG telemetry units was performed as previously described. EEG data were acquired with EEG transmitters (Model:F20-EET. Data Systems International) configured to record 2-channel EEC that were skull-affixed over dorsal hippocampi and temporal cortex under anaesthesia at the time of surgery for intra-amygdala injection. Transmitter units were placed in a subcutaneous pocket along the dorsal flank. Continuous (24 h per day) EEG data were collected for 14 consecutive days after SE. EEC data were reviewed and manually scored by an observer unaware of experimental treatment with epileptic seizures defined as high frequency (>5 Hz) high amplitude (>2×baseline) polyspike discharges of ≥5 s duration.

Mouse Model of Ischaemia-Induced Brain Injury:

Focal cerebral ischaemia is performed on C57BL/6 male mice (20-25 g). All procedures are under general anaesthesia. Temporary focal ischemia is induced using the technique of Longa et al. (1989), with modifications. Briefly, animals are anesthetized with 3-5% isoflurane. Endotracheal intubation is performed and animals are ventilated mechanically by a rodent ventilator. Rectal temperature is maintained at 36-38° C. with a heat lamp. Following an incision in the throat, under an operating microscope, the bifurcation of the common carotid artery is exposed, and the external carotid artery ligated. The internal carotid artery (ICA) is isolated, the extracranial branch of the ICA is ligated, and then a suture (e.g. nylon) is introduced into the lumen of the ICA and advanced to occlude the MCA (~10 mm). Reperfusion is achieved 60-90 min later by withdrawal of the suture.

For intracerebroventricular (i.c.v.) administration of antagomir, the mice are affixed with au additional cannula (Coordinates from Bregma: AP=−0.3 mm, L=−1.0 mm, V=−2.0 mm) ipsilateral to the side of MCA occlusion. Scrambled or miRNA-184 antagomirs (0.12 nmol) (Exiqon, LNA- and 3'-cholesterol modified oligonucleotides) are infused in a volume of 2 μl artificial cerebrospinal fluid (aCSF). Antagomirs are injected either 24 h before stroke or 1 h after.

The primary measure of efficacy is assessed in coronal sections of the mouse brain using TTC or nissl-stained sections. Sensory-motor deficits is a secondary functional measure reduced volume of ischemic infarction. These experiments test whether administration of an antagomir of miR-134 cause prevent or reduce damage to the brain caused by ischaemic infarction.

Data Analysis.

Data represents the mean±standard error of the mean (s.e.m.). Two group comparisons were made using un-paired Student's t-test, while multi-group comparisons were made using one or two-way analysis of variance (ANOVA) followed by appropriate post hoc testing (GraphPad Instat). Significance was accepted at $P<0.05$.

Results miR-134 and Target Limk1 are Regulated by SE and in Epilepsy

Prolonged seizures (SE) were triggered by intra-amygdala microinjection of the glutamate receptor agonist kainic acid (KA) in mice. The resultant seizures recruit limbic brain regions, cause hippocampal damage and trigger the eventual emergence of recurrent spontaneous (i.e. epileptic) seizures. As before, SE caused neuronal death mainly within the CA3 subfield and hilus of the ipsilateral hippocampus (FIG. 1a).

The in vivo cell populations expressing miR-134 were identified using in situ hybridisation. Staining of hippocampus using proves specific for mature miR-134 detected a strong signal in the soma of pyramidal neurons, as well as other neuronal populations (FIG. 1b). Real-time quantitative PCR (RT-qPCR) analysis showed SE led to an increase in expression of mature miR-134 levels in both the CA3 and CA1 subfields of the hippocampus (FIG. 1c). To determine if this change was specific to harmful/damaging seizures, miR-134 levels were measured after non-harmful, non-conclusive seizures in a second model in which KA was given as a low-dose systemic injection (a model of seizure-preconditioning). RT-qPCR analysis determined miR-134 levels (relative to the small nuclear RNA. U6B) were not significantly changed (CA3:Vehicle 1.19±0.27, KA 1.24±0.18 (P-0.89) and CA1:Vehicle 1.16±0.05, KA 1.25±0.15 (P=0.56) (n=6 per group)).

To determine whether miR-134 was functions, levels of miR-134 were measured within the RISC, where targeting of miRNAs to mRNA occurs. Using a pull-down assay approach known to one skilled in the art, Argonaute-2 was eluted from CA3 and miRNA was extracted. There was a low level or miR-134 in association with Argonaute-2 in control CA3, whereas levels of Argonaute-2-bound miR-134 were increased after SE (FIG. 1d). As an additional measure of miR-134 functionality, Limk1 was examined. Protein levels of Limk1 were significantly lower in mice after SE (FIG. 1e).

miR-134 and Limk1 expression levels were examined in experimental epilepsy. Spontaneous seizures emerge 3-4 days after SE in the model used herein and by two weeks thereafter, animals display pathologic hallmarks of temporal lobe epilepsy, including neuron loss and astrogliosis (FIG. 1f). Mature miR-134 levels were elevated in the CA1 and CA3 subfields of epileptic mice (FIG. 1g). Protein levels of Limk1 followed an opposite pattern to miR-134, displaying a decrease in epileptic animals (FIG. 1h). An analysis of the temporal lobe material from human patients with pharmacoresitent epilepsy revealed higher levels of mature miR-134 in surgically-obtained temoporal lobe resection specimens from epilepsy patients compared to autopsy controls (Figure Protein levels of Limk1 were lower in temporal lobe epilepsy patients than in autopsy controls (FIG. 1i).

In Vivo Depletion of miR-134 Using Antagomirs

Figure 2:
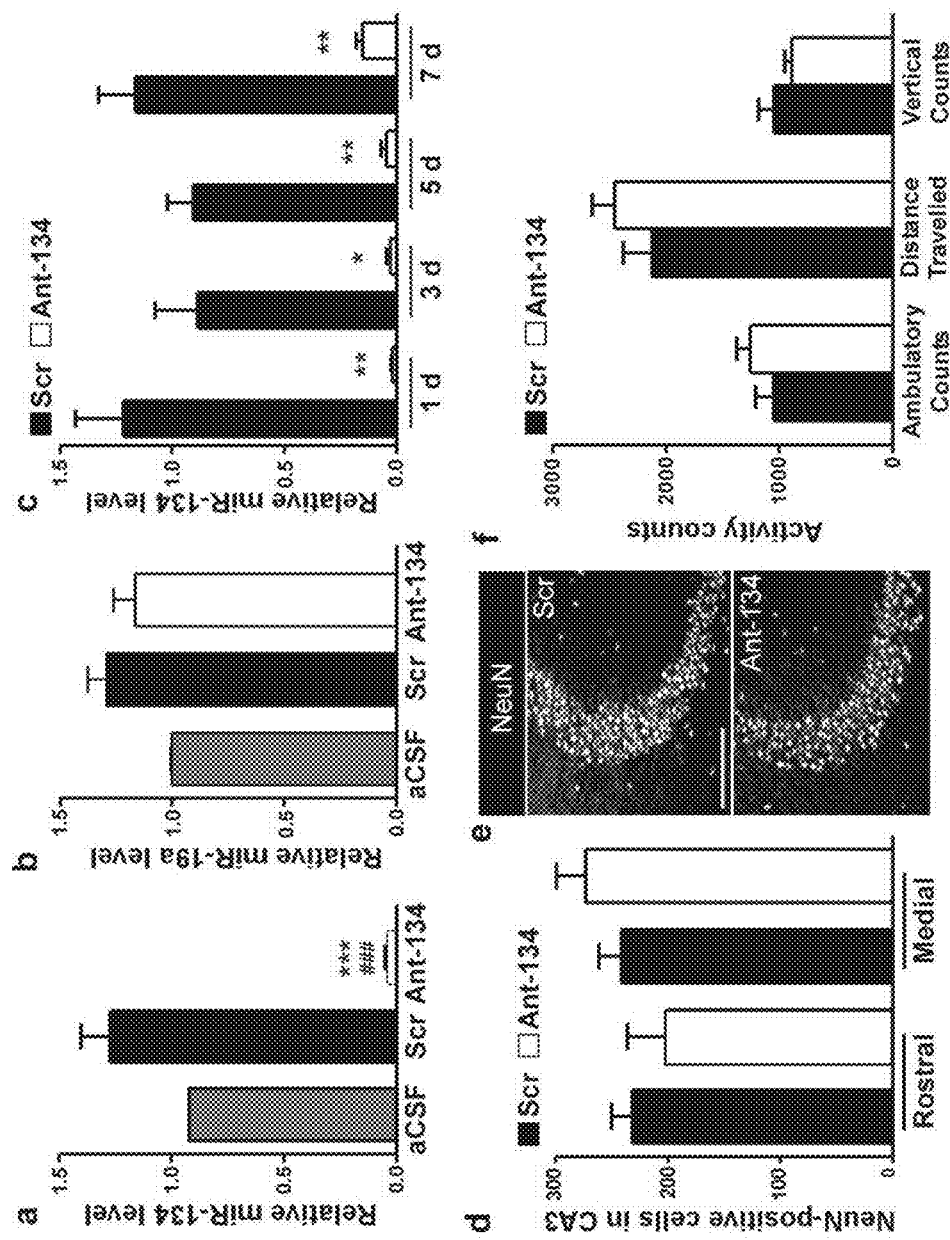
FIG. 2 Antagomir-mediated silencing of miR-134 in mouse hippocampus. (a-b) RT-qPCR measurement of a) miR-134 (P<0.001) and b) miR-19a (P=0.363) in hippocampus 24 hr after i.c.v. injection of miR-134 targeting antagomir (Ant-134) or a non-targeting control (Scr). ***P<0.001 compared to artificial cerebrospinal fluid (aCSF); ###P<0.001 compared to Scr (n=3 per group). (c) RT-qPCR measurement of miR-134 levels in hippocampus after injection of Ant-134 or Scr at 1 (P=0.005), 5 (P=0.001) and 7 (P=0.004) days later. *P<0.05; ##P<0.01 (n=3 per group). (d) NeuN counts at two different levels of the hippocampus in animals injected 24 hr earlier with either Scr or Ant-134 (rostral, P=0.585; medial, P=0.387) (n=4 per group). (e) NeuN staining CA3 at 24 hr in animals injected with either Scr or Ant-134. (f) Behavioural analysis of mice injected 24 hr earlier either with Scr or Ant-134. No significant differences were observed between groups across the following indices of exploratory activity; total ambulatory counts (P=0.310); distance travelled (cm) (P=0.320); vertical counts (P=0.300). Scale bar: e, 200 μm.
Figure 7:
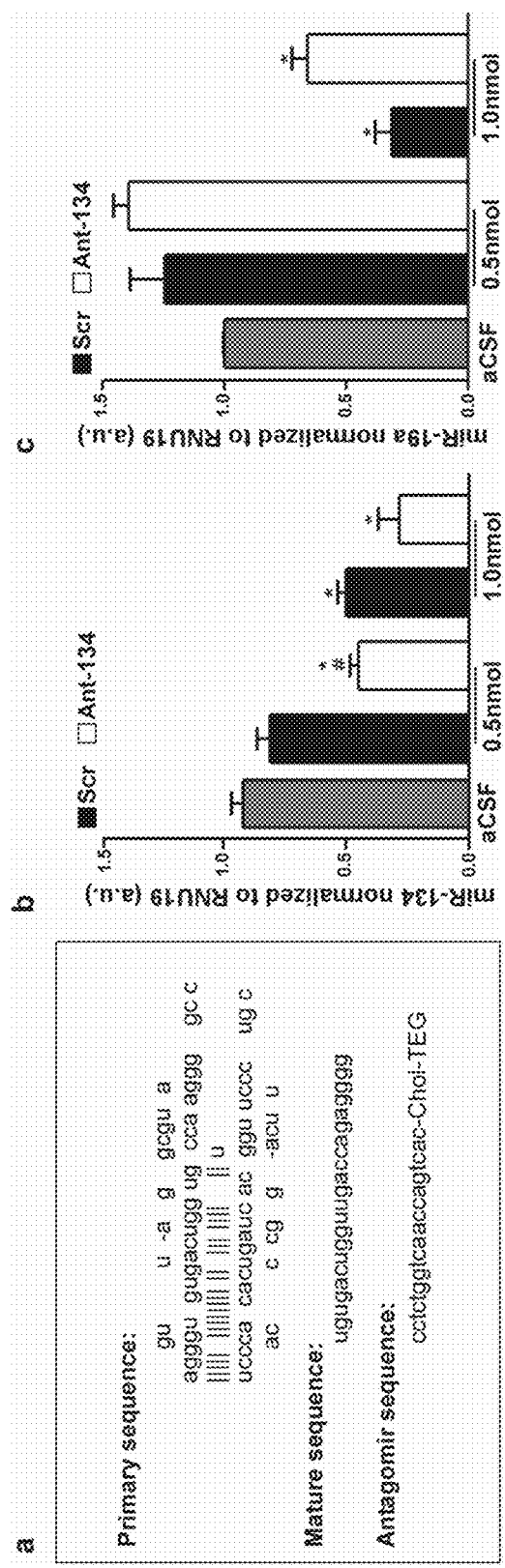
FIG. 7 miR-134 targeting by antagomirs.

Mice were injected with locked nucleic acid 3' cholesterol-conjugated oligonucleotides ("antagomirs"). Antagomirs targeting miR-134 (Ant-134) or a non-targeting scrambled sequence (Scr) were injected into the mouse ventricle (i.c.v.) and miRNA silencing was confirmed by RT-qPCR 24 hr later (FIG. 7). Injection of 0.12 nmol Ant-134 reduced hippocampal levels of miR-134 by over 95% (FIG. 2a). Hippocampal levels of an unrelated miRNA, miR-19a, were not changed in Ant-134-injected animals (FIG. 2b). At much higher doses, off-target knockdown of miRNAs were noted for both targeting and non-targeting antagomirs. To determine who long miR-134 silencing persisted after a single antagomir injection, hippocampal miR-134 levels were analysed up to one week after injection of Ant-134 or Scr. miR-134 levels remained suppressed 7 days after injection, although levels showed as small recovery during this time frame (FIG. 2c). Brain from mice injected with antagomirs had grossly normal anatomy. There was no evidence of hippocampal neuronal death found when sections from mice injected with antagomirs were stained with Fluoro-Jade® B, DNA fragmentation (TUNEL), and the neuronal marker NeuN (FIG. 2d,e).

A series of ethological tests were carried out to determine if reduction in the levels of miR-134 had any gross effects on animal behaviour. Mice were injected with either Scr or Ant-134 and assessed 24 hr later. No differences in ambulatory counts, distance travelled or vertical counts were found between groups (FIG. 2f), suggesting silencing, of miR-134 does not alter normal exploratory activities.

Figure 3:
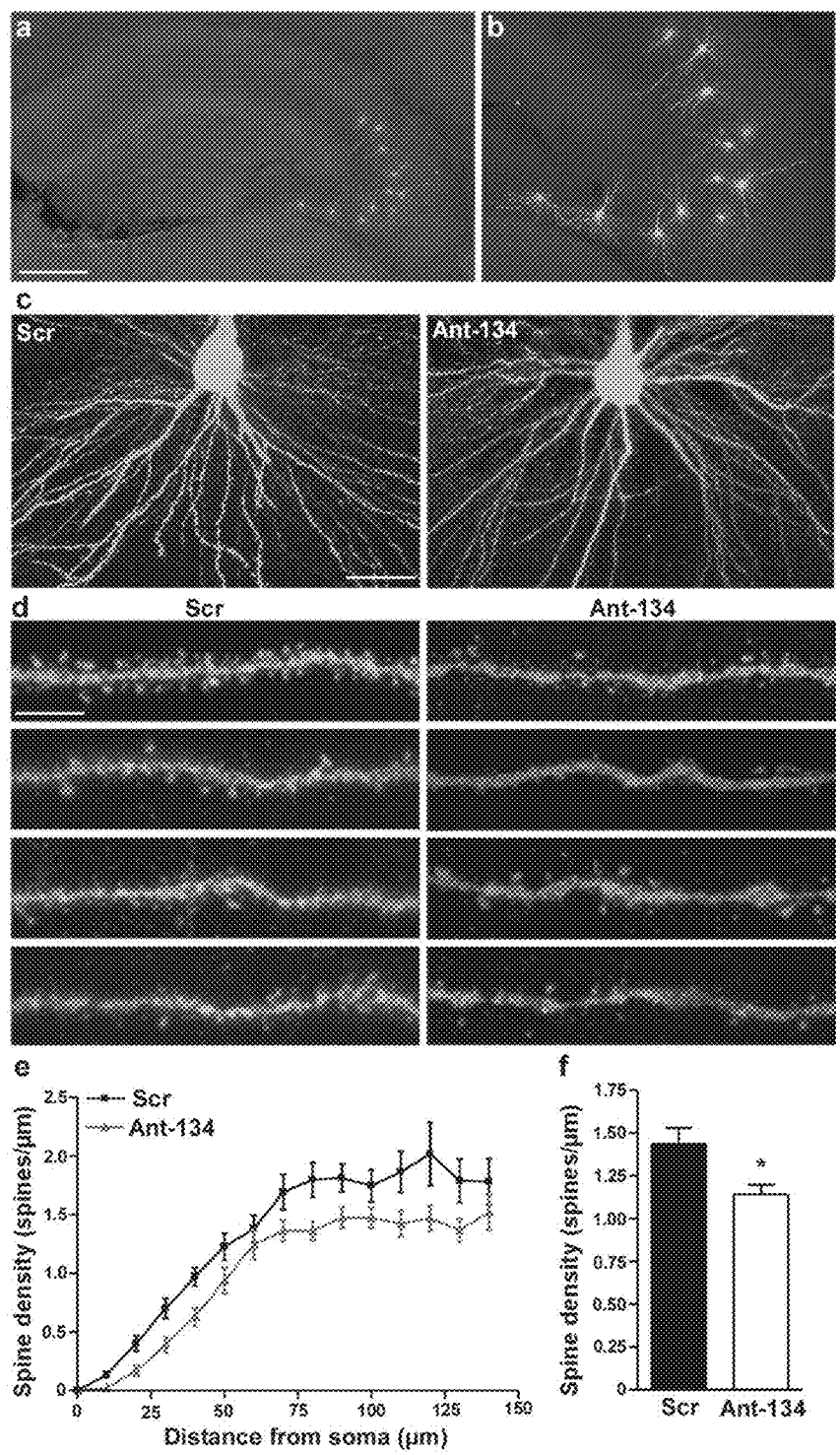
FIG. 3 Antag-134 reduces hippocampal CA3 spine density in vivo. (a) Field view of hippocampus showing Lucifer yellow-injected CA3 neurons (green) and nuclei (DAPI, blue). (b) Higher magnification of (a) to illustrate injected CA3 neurons. (c) Photomicrographs of the basal tree from Lucifer yellow-injected animals treated with either Scr or Ant-134 24 hr earlier. (d) Representative images of individual dendrites from four individual animals injected with Scr (left panels) or Antag-134 (right panels). (e) Spine density as a function of the distance from the soma (Sholl Analysis) for Scr and Antag-134 animals. (f) Spine density in Scr and Antag-134 mice (P=0.037; *P<0.05 compared to Scr, n=7 per group). Scale bars: a, 50 μm; b, 100 μm; c, 20 μm; d. 12 μm.

Antagomir Silencing or miR-134 Reduces CA3 Pyramidal Neuron Spine Density In Vivo As in vitro and in vivo evidence supports a role for miR-134 in controlling dendritic spine morphology, it was determined whether antagomirs caused changes to dendritic spines in vivo. Individual CA3 pyramidal neurons in hippocampal slices from mice given Ant-134 or Scr 24 hr earlier were microinjected with Lucifer Yellow and imaged using conformal microscopy (FIG. 3a,b). Two-hundred eighteen neurons in Scr Mice (n=7) and 181 neurons in Ant-134 mice (n=7) were analysed. The structure of the basal dendritic tree was grossly normal between groups, as was the distribution of spines (FIG. 3c). Dendrites from Scr mice had an average of 68 nodes (ramifications) compared to 72 nodes in Ant-134 animals. The number of ramification points per μm was also similar (0.0127 nodes per μm in Scr compared to 0.0131 nodes per μm in Ant-134). Spine density analyses was performed, assessing a total of 5343.7 μm length of dendrites in Scr mice (7455 spines) and a similar length (5477.5 μm) in Ant-134 animals (6196 spines). Spine density was 21% lower in antag-miR-134 mice compared to Scr-injected animals (FIG. 3d-f). Thus, silencing miR-134 using antagomirs results in a significant reduction in spine density in vivio.

miR-134 Silencing Inhibits SE and Seizure-Induced Neuronal Death In Vivo

Figure 4:
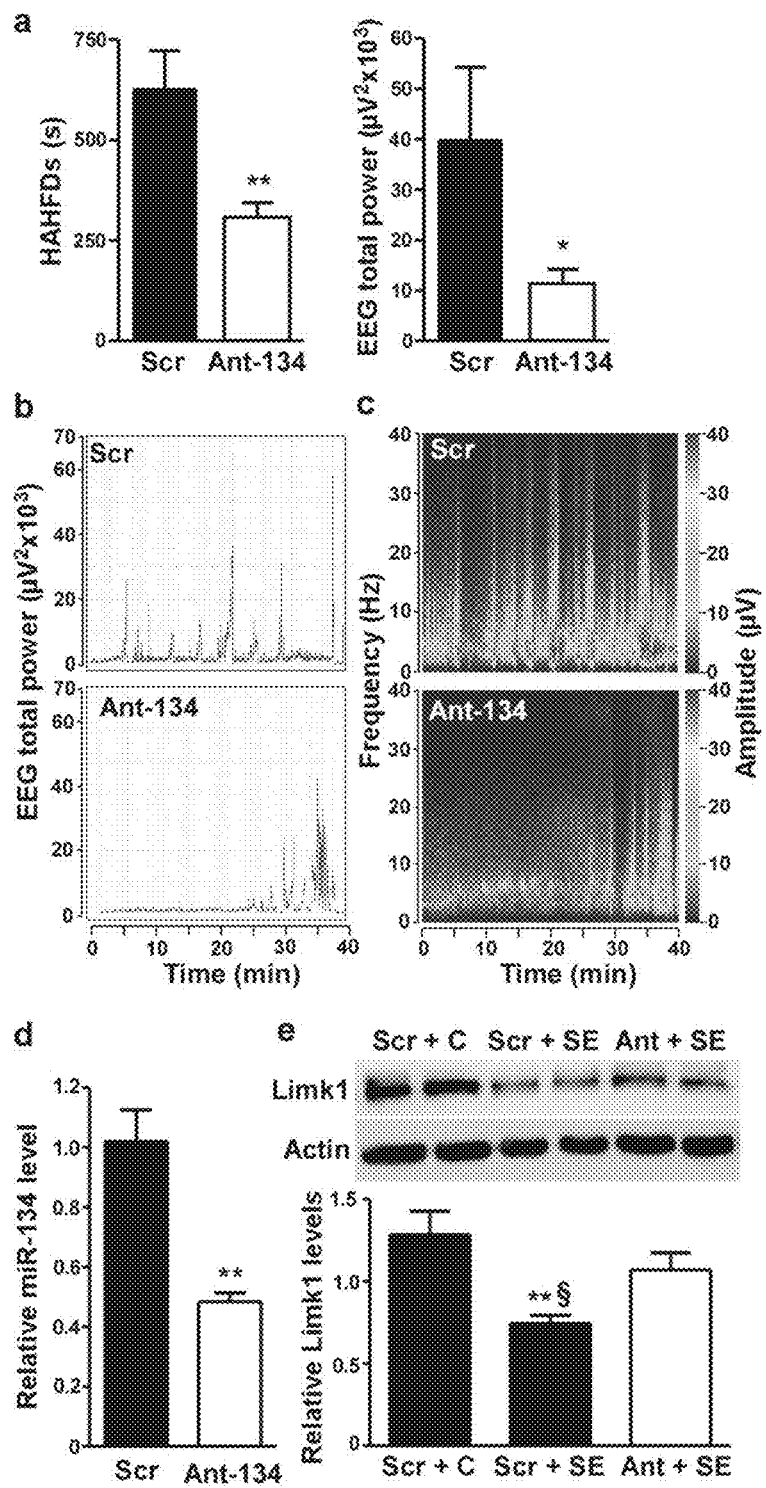
FIG. 4 Antagomir silencing of miR-134 reduces seizure severity during SE. (a) EEG parameters during SE in animals injected 24 hr earlier with Scr or Ant-134 (n=4-8 per group). Antag-134 reduced high amplitude and high frequency discharges (HAHFDs) (P=0.0051) and total EEG power (P=0.033). (b) Total EEG power and (c) frequency and amplitude parameters during SE from representative Scr- and Antag-134 injected animals covering the period between KA injection and anticonvulsant administration. (d) RT-qPCR measurement of miR-134 levels in Scr and Antag-134 animals 24 hr after SE (P=0.0078, n=4). (e) Limk1 protein expression in non-seizure, Scr-injected (Scr+C) and after SE in mice given Scr (Scr+SE) or Antag-134 (Ant+SE) (n=1 per lane). Graph shows Limk1 levels normalised to actin (Scr-t-C compared to Scr+SE, P=0.007; Scr vs Antag-134 after SE (P=0.018; Scr+C compared to Antag-134+SE, P=0.270). **P<0.01 compared to Scr+C; §P<0.05 compared to Antag-134+SE) (N=4 per group)).
Figure 8:
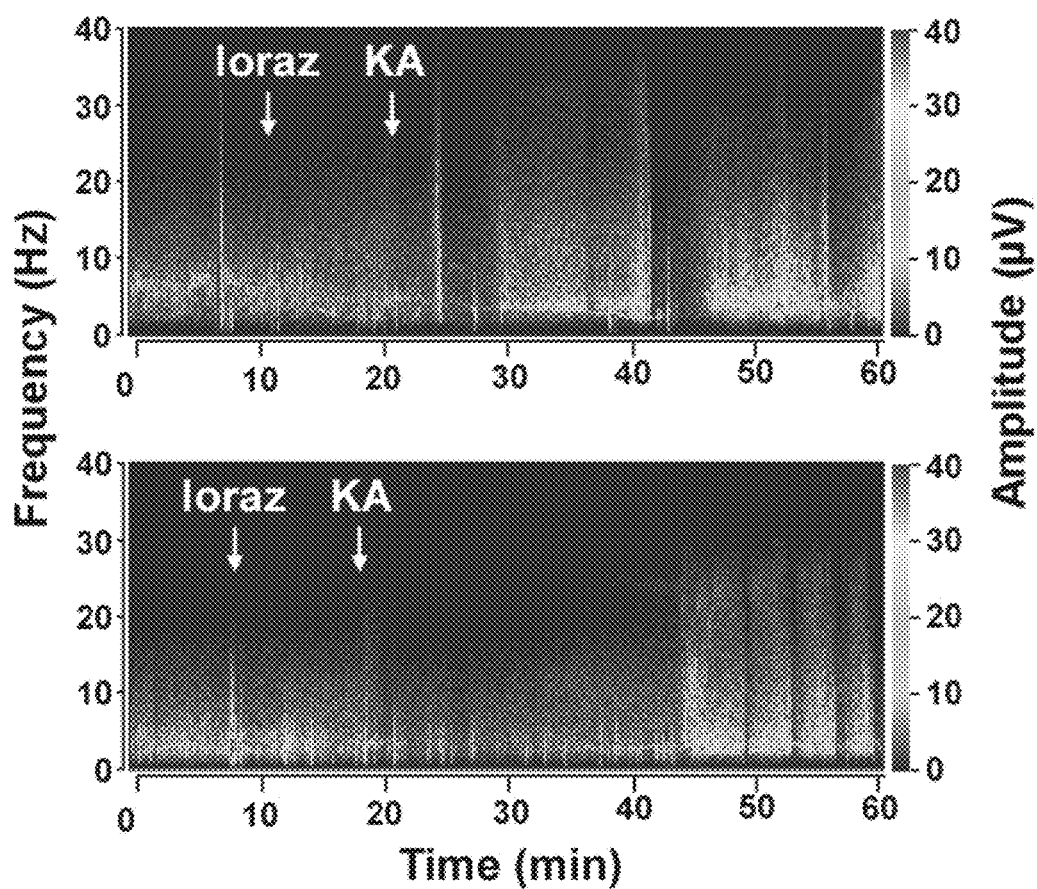
FIG. 8 Effect of lorazepam pre-treatment on status epilepticus. As a guide to the seizure-suppressing effect of Ant-134, additional mice (n=3) were pre-treated with lorazepam (Loraz; 6 mg/kg, i.p.) 10 min before intra-amygdala KA injection.

To test the idea that antagomirs might influence pathologic brain activity in vivo, seizures evoked by intra-amygdala KA between mice injected 24 hr earlier with either Scr or Antag-134 were compared (FIG. 4a). Scr-injected mice experienced typical SE, comprising episodes of high amplitude high frequency discharges (HAHFDs) which lasted approximately 600 seconds during the course of the experiments; these durations are similar to those reported in the model previously. Quantitative EEG analysis revealed the duration of HAHFDs, which are associated with damage-causing pathologic activity, and total EEG power, to be strongly reduced in Ant-134-injected mice (FIG. 4a-c). As an indicator of the degree of seizure-suppression, this was quantitatively similar to the reduction observed in animals when lorazepam was given 10 minutes before KA (FIG. 8).

RT-qPCR confirmed miR-134 levels were reduced after SE in mice injected with Ant-134 compared to Scr-treated animals (FIG. 4d). Limk1 protein levels were lower after SE in Ser-injected mice whereas Limk1 levels were higher in mice injected with Ant-134 (FIG. 4e).

Hipocampal damage in tissue sections from Scr- and Ant-134 mice were examined. Scr-injected mice displayed a typical CA3 lesion 24 hr after SE, with extensive staining of neurons for Fluoro-Jade® B and TUNEL and loss of NeuN staining (FIG. 5a-f). Mice injected with Ant-134 before SE showed a dramatic reduction in each measure of seizure-induced neuronal death (FIG. 5a-f).

Figure 5:
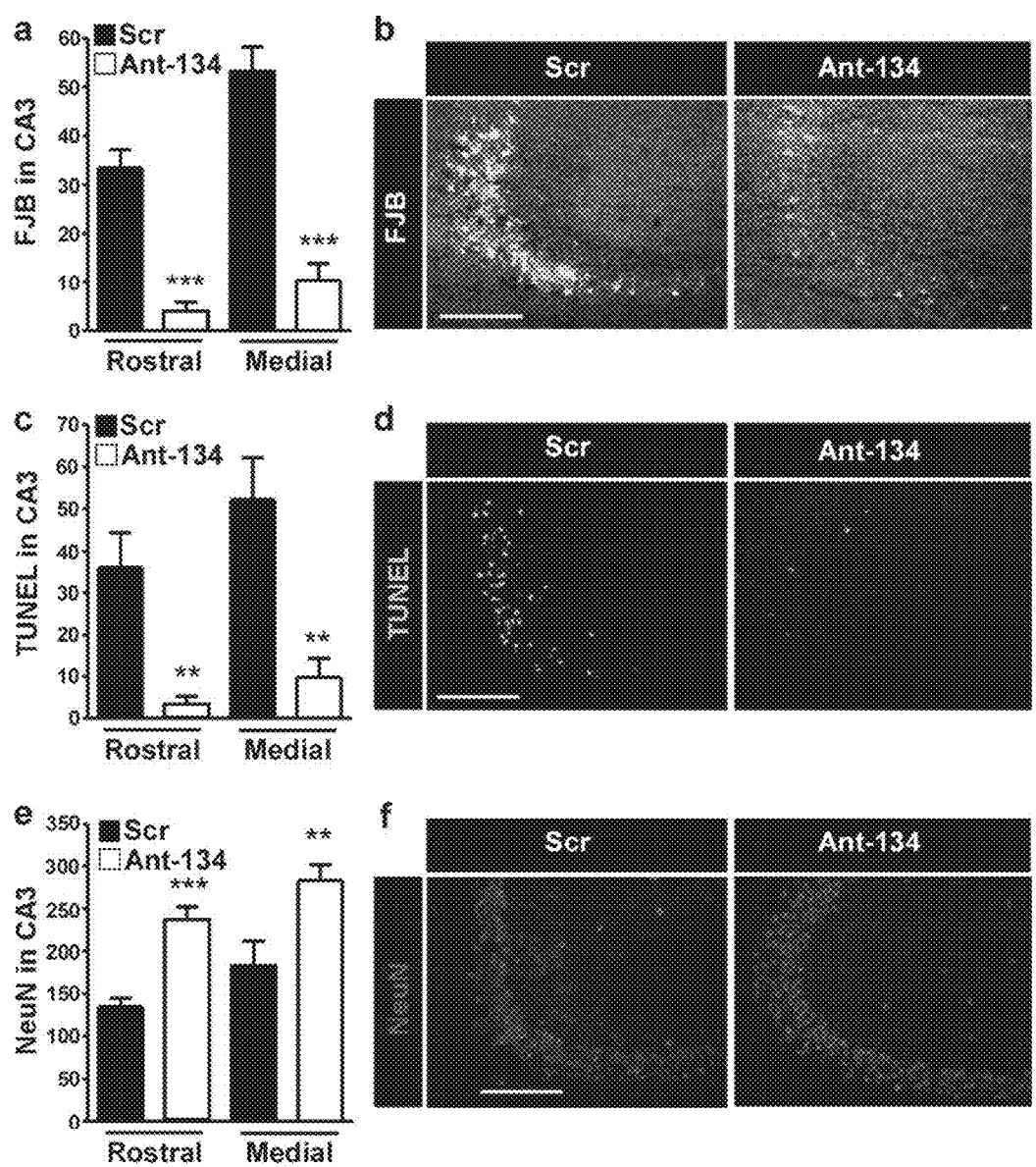
FIG. 5 Antagomir silencing of miR-134 protects against SE. (a,b) Graphs and representative photomicrographs showing Antag-134 reduced FJB counts in CA3 24 hr after SE at both a rostral (P<0.001) and medial (P<0.001) level of the dorsal hippocampus compared to Scr. (c,d) Graphs and representative photomicrographs showing Antag-134 reduced TUNEL in rostral (P=0.001) and medial (P=0.001) levels of dorsal hippocampus. (e,f) Graphs and representative photomicrographs showing Antag-134 increased numbers of NeuN-positive cells compared to mice given Scr at level of rostral (P<0.001) and medial (P=0.009) dorsal hippocampus. P<0.01, *P<0.001 compared to Scr (n=4-8 per group). Scale bars: b, d, e 200 μm. (g) miR-134 levels in primary hippocampal neurons 24 h after KA (0.3 μM) (P=0.019). *P<0.05, n=3 per group. (h) Western blots show Limk1 and GFP in SH-SY5Y cells transfected with shControl (Con) or different short interfering RNAs targeting Limk1 (shLimk1/2). shLimk2 reduced Limk1 by ~48% (average of two experiments), (i) Percentage cell death induced by KA in hippocampal neurons (ratio of propidium iodide (PI) positive-GFP positive neurons over GFP-positive), and effect of Scr or Ant-134 in cells co-transfected with either Con or Limk shRNA. Cell death in non-transfected neurons in either group averaged 30±12% (data not shown). shCon/Scr compared to shCon/Ant-134, P=0.005; shLimk/Sec compared to shCon/Ant-134, P=0.004; shCon/Ant-134 compared to shLimk/Ant-134. P=0.001). **P<0.01, n=4 per group. (j) Photomicrographs of hippocampal neurons in each condition. Arrows (and see inset) indicate dead cells positive for both GFP (green) and PI (red). Scale bar, 50 μm.
Figure 5:
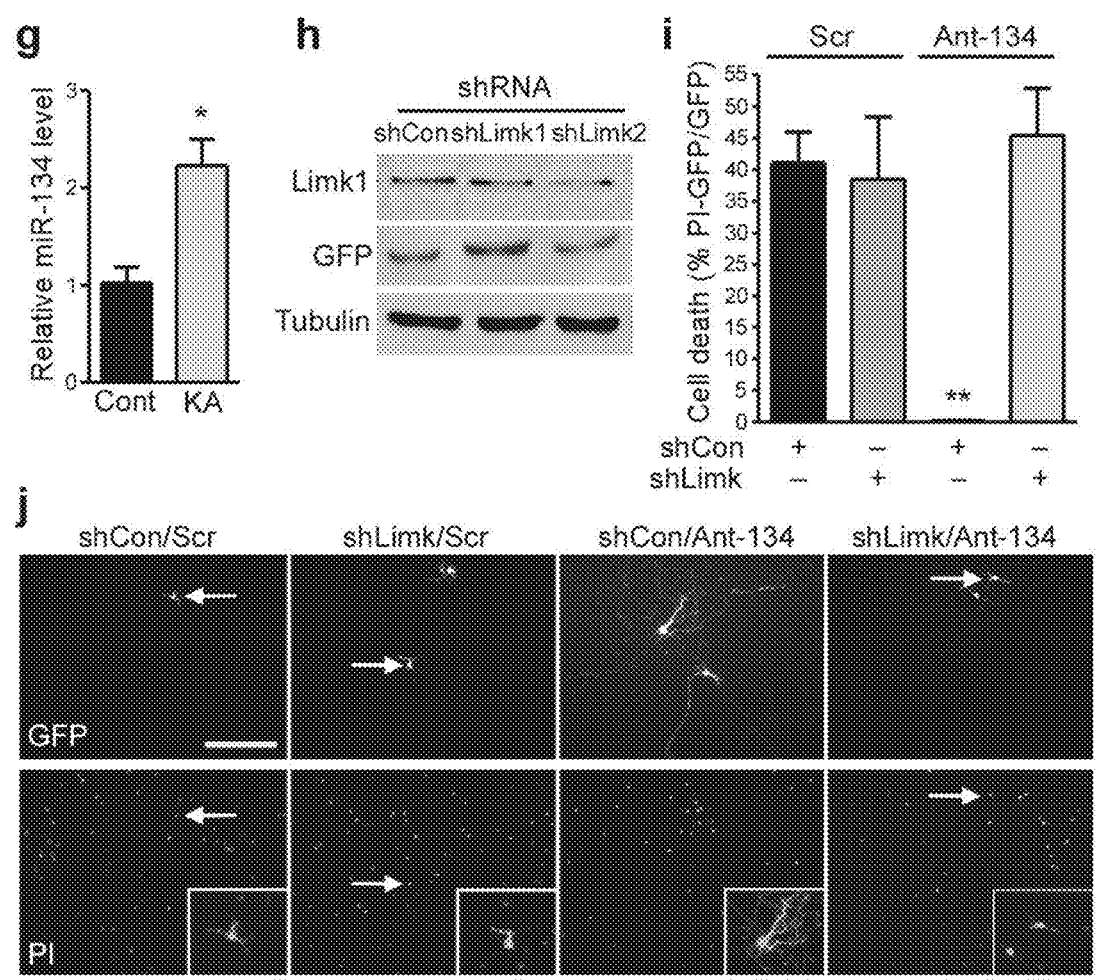

To specifically link the neuroprotective effects of antagomirs to miR-134 and Limk1, cultures of primary hippocampal neurons were treated with KA to model excitotoxic injury, the core pathophysiologic component of stroke. Treatment with KA increased miR-134 levels (FIG. 5g). Ant-134 prevented KA-induced neurotoxicity in hippocampal neurons, and this was blocked in neurons transfected with short-hairpin RNAs targeting Limk1 (FIG. 5h-j).

Silencing of miR-134 Prevents Spontaneous Recurrent Seizures

Figure 6:
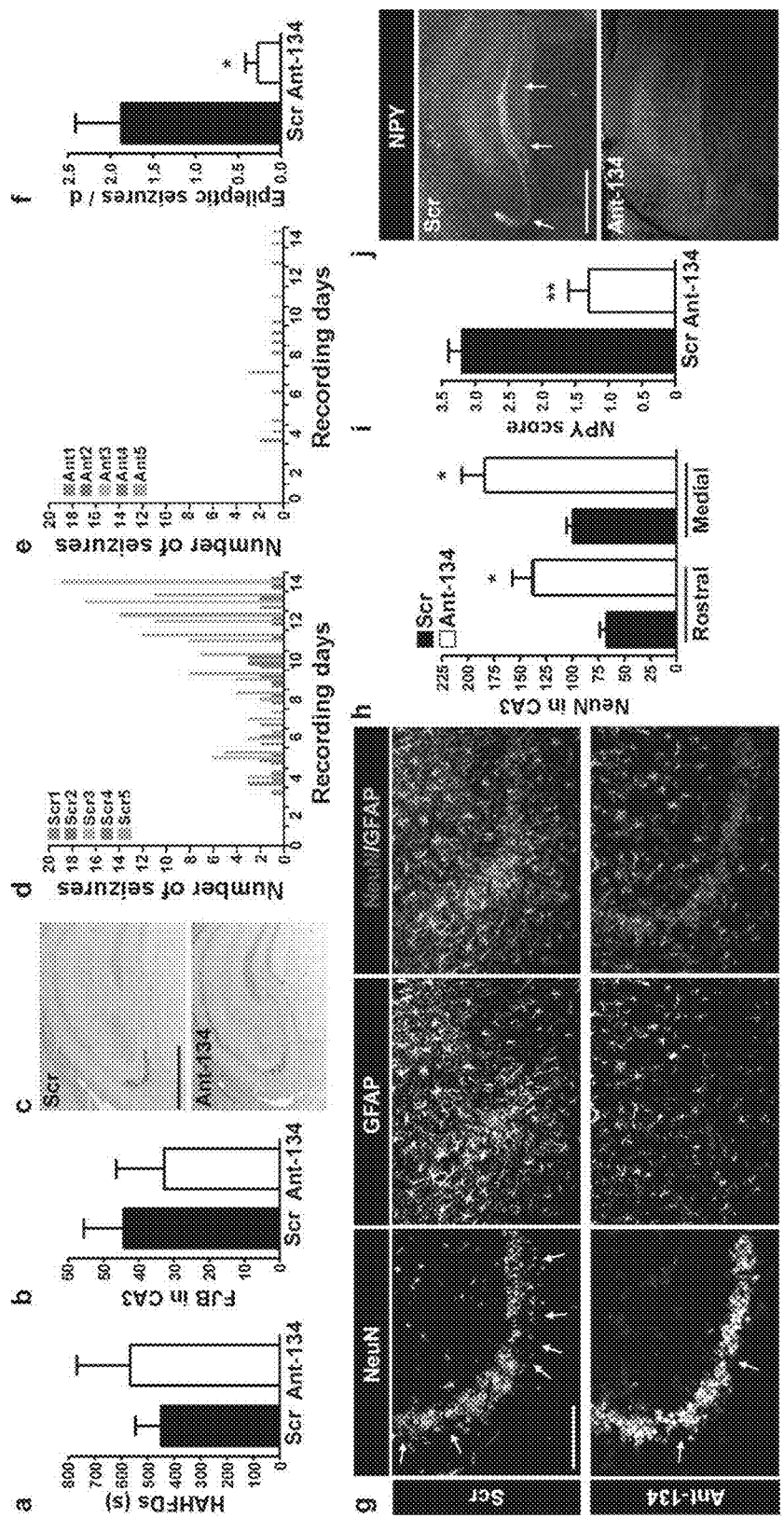
FIG. 6 Antagomir silencing of miR-134 is anti-epileptogenic and protects against progressive features of temporal lobe epilepsy. (a,b) Graph shows a) seizures (P=0.589) and b) CA3 damage at 24 hr (P=0.541) was not different between Antag-134 and Scr groups when the antagomirs were injected 1 hr after triggering SE. (n=4-5 per group). (e) FJB staining is similar in the ipsilateral CA3 of mice injected with Scr or Antag-134 beginning 1 hr after KA. (d,e) Graphs show the number of spontaneous seizure each day for individual animals during the two weeks following SE for d) Scr and e) Antag-134 mice. (f) Graph shows average daily epileptic seizure number in Scr and Antag-134 animals (P=0.036, n=5 per group). The duration of individual epileptic seizures were similar (P=0.610, not shown). (g) Photomicrographs showing NeuN and GFAP in Scr and Antag-134 mice after epilepsy monitoring for two weeks, depicting the greater neuron loss and astrogliosis in CA3 in Scr animals compared to Antag-134. (h) NeuN counts in rostral and medial levels of the dorsal hippocampus (rostral, P=0.024, medial, P=0.02) (*P<0.05, n=5 per group). (i) Neuropeptide Y (NPY) score in epileptic animals (P=0.008, N=5 per group). (j) NPY stained sections from Scr and Antag-134 mice after epilepsy monitoring for two weeks. Scale bars: g, 200 µm; j, 1 mm. (k) Graphs show the number of generalized tonic-clonic seizures (GTCS) each day for individual animals during two periods of five days continuous video monitoring following SE for (left) Scr and (right) Ant-134 mice, (l) Total GTCS counts averaged from the two monitoring periods (**P=0.003, n=5-6 per group).
Figure 6:
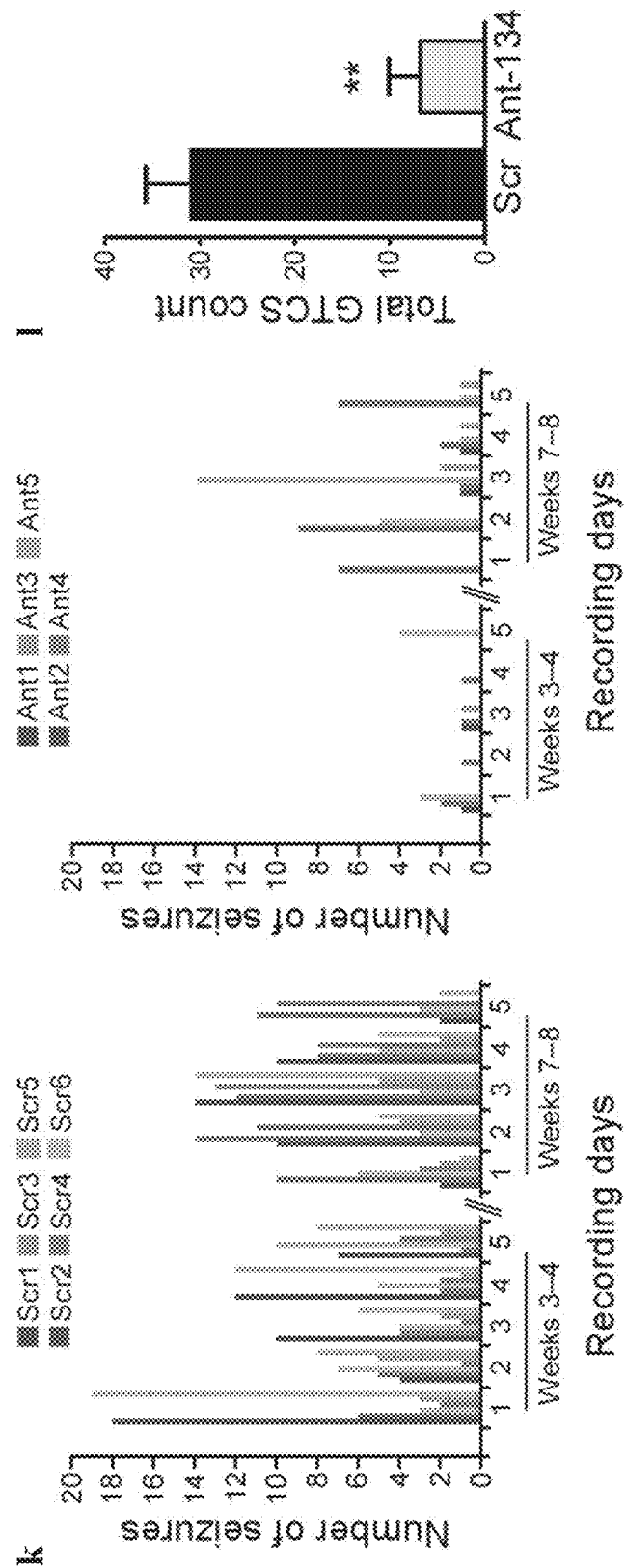

Antagomirs were injected after SE, allowing to test whether miR-134 silencing could impact epileptogenesis without confounding influences of seizure-suppression and neuroprotection. Analysis of EEC confirmed that when antagomirs were injected 1 hr after KA, there was no difference in SE between Ant-134 and Scr groups (FIG. 6a). Also, Ant-134 injection after SE had no effect on neuronal death in the CA3 subfield when assessed 24 hr later (FIG. 6b,c) Continuous 24 hr/day EEG recording with mice equipped with EEC telemetery units for two weeks following SE revealed that mice injected with Scr after SE experienced their first spontaneous seizures on the third day, and all mice were epileptic by day 4 (FIG. 6d,f and FIG. 9). The median epileptic seizure count for Scr-injected mice was 25 (range 8-79), with 200 epileptic seizures recorded in total (FIG. 6d and FIG. 9). In contrast, only 607) of mice injected with Ant-134 had had a spontaneous seizure by the eleventh day after SE (FIG. 6e and FIG. 9); one mouse had only a single seizure on day 14 and another had no seizures (FIG. 6e). Ant-134-injected mice had a median epileptic seizure count of 2 (range 0-7), with just 16 epileptic seizures detected in total during the two week recording period (P=0.001, two-way ANOVA compared to Sec group) (FIG. 6f). Total amount of time spent in seizures also differed between the groups (P<0.001, two way ANOVA).

Silencing miR-134 Alters Pathologic Hallmarks of Temporal Lobe Epilepsy

Progressive neuron loss, gliosis and rearrangement of mossy fibers are common pathological hallmarks of temporal lobe epilepsy. It was examined whether silencing miR-134 had altered underlying pathology in these epileptic mice. Neuron counts in Ant-134-injected mice were significantly higher than Scr-treated animals at the endo f epilepsy monitoring (FIG. 6g,h), and astrogliosis was reduced (FIG. 6g). Neuropeptide Y staining, which is upregulated within mossy fiber terminals in epileptic animals, was scored as an index of increasing organisation of the hippocampus. Neuropeptide Y scores in Scr-treated mice (FIG. 6i,j) were similar to previously reported scores in epileptic mice. In contrast, Neuropeptide Y scores in An-134 mice were significantly lower (FIG. 6i,j).

Figure 11:
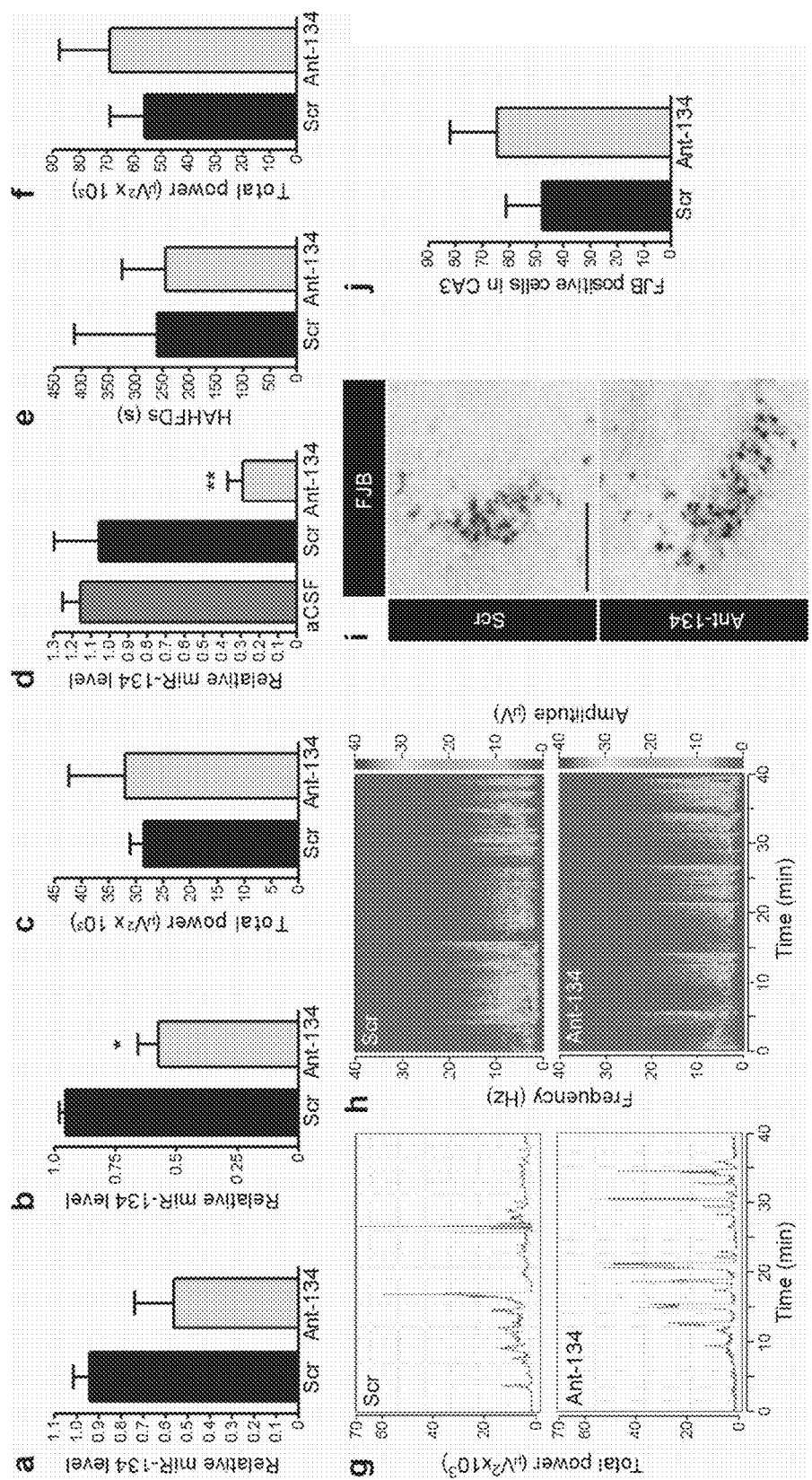
FIG. 11 Experiments on the issue of prolonged anticonvulsive versus anti-epileptogenic effects of antagomirs. (a) miR-134 levels in hippocampus of telemetry mice, 14 days after SE. Levels of miR-134 in Ant-134 animals were ~55% of levels in Scr mice (P=0.07, n=5 per group). (b) miR-134 levels 24 h after intranasal Ant-134 (0.12 nmol per nostril). The reduction in miR-134 levels matched that detected in Ant-134-treated mice at the end of epilepsy monitoring (~55% of Scr level; P=0.02). *P<0.05, n=4 per group. (c) Total EEG power during SE in mice was not different between groups treated 24 h earlier with intranasal administration of Scr or Ant-134 (P=0.755, n=4 per group). Thus, lowering miR-134 levels to ~55% of Scr does not have an anticonvulsant effect in this model. (d) Levels of miR-134 in hippocampus 14 days after i.c.v. injection of aCSF. Scr or Ant-134 (0.12 nmol) (P=0.005).**P<0.01, n=3 per group. (e, f) Graphs show (e) HAHFDs, and (f) total EEG power, during SE in mice injected i.c.v. with Scr or Ant-134 14 days previously (HAHFDs; P=0.924; Total EEG power: P=0.538; n=5 per group). As with the intranasal route, this reduction in miR-134 levels was insufficient to have an anticonvulsant effect. Representations of (g) total EEG power and (h) frequency and amplitude parameters during SE from animals given Scr- or Ant-134 14 days before SE. Recorded period covers time between KA injection and anticonvulsant administration. (i, j) FJB staining and counts in CA3 between Scr and Ant-134 mice when i.c.v. injections were performed 14 days prior to SE (P=0.467, n=4 per group). Scale bar, 170 µm.

To investigate whether the reduced epileptic seizure rates were due to an anti-epileptogenic effect or a prolonged anticonvulsant effect of Ant-134, miR-134 levels were measured in Ant-134 mice at the end of 14 days of telemetry recordings, which established levels were ~55% of those in Scr-injected animals (FIG. 11a). Modeling this miR-134 reduction in mice did not produce an anticonvulsant effect against KA-induced SE (FIG. 11b, c). Likewise, when Ant-134 was injected 14 days before KA this reduced levels of miR-134 to ~70% of Si but mice were normally sensitive to KA-induced SE (FIG. 11e-h), and animals were not protected against SE-induced damage (FIG. 11i,j). Finally, longer-term video monitoring revealed mice given Ant-134 after SE displayed fewer generalized tonic-clonic seizures and more seizure-free days up to two months later compared to Scr-injected animals, although seizure rates did increase in 3 out of 5 animals (FIG. 3k,l).

The Applicant has demonstrated herein that silencing miR-134 in vivo profoundly suppresses evoked seizures and dramatically reduces the occurrence of spontaneous seizures and associated pathologic hallmarks of epilepsy. The inhibition of a single mature miRNA alters the pathologic electrical activity in brain. mRNA silencing experiments described herein support a role in facilitating pathologic neuronal activity in vivo because seizures were potently suppressed in animals in which miR-134 was depleted by antagomirs. The seizure-suppressing effect of miR-134 knockdown was unexpectedly large, and nearly comparable to benzodiazepines. The hippocampus was also protected against damage when miR-134 antagomirs were given before SE. miR-134 expression was increased in both experimental and human epilepsy, and silencing miR-134 after SE resulted in near-complete prevention of epileptic seizures in mice. Epilepsy developed normally in Scr-injected mice, whereas spontaneous seizures seldom occurred in Ant-134-treated animals. Thus, the effect was superior to neuroprotection applied at the time of SE. Indeed, overt neuroprotection was excluded as a potential mechanism by injecting antagomirs after SE. The results are comparable or exceed the performance of several other experimental anti-epileptogenic treatments (see Pitkanen and Lukasiuk "Mechanisms of epileptogenesis and potential treatment targets". *Lancet Neurol.* Vol 10, pages 173-186 (2011)). Silencing of miR-134 was not associated with obvious toxicity in low doses. The longevity of the suppression after a single injection suggests applications in refractory epilepsy or disease-modification in the wake of epilepsy-precipitating injuries. Taken together, this data demonstrates that miR-134 antagomirs have disease-modifying effects and can offer an approach to anti-epileptogenesis.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

We claim:

1. A method for treating epilepsy or status epilepticus in an individual comprising administering an agent for inhibiting the activity of miR-134 to the individual, wherein the agent is delivered to the brain of the individual.

2. The method of claim 1, wherein the agent for inhibiting the activity of miR-134 is a specific low molecular weight inhibitor of miR-134 expression selected from an anti-sense molecule, a siRNA molecule, a shRNA molecule, a micro-RNA sponge, and a decoy oligonucleotide.

3. The method of claim 2, wherein the anti-sense molecule is an antagomir or a tiny seed target LNA oligonucleotide.

4. The method of claim 3, wherein the agent is a miR-134 antagomir.

5. The method of claim 4, wherein the anti-sense molecule has a sequence selected from SEQ ID NO: 5 or SEQ ID NO: 7.

6. A method for inhibiting the development or reducing occurrence of seizures in an individual having a brain-related disorder characterized by development of seizures comprising administering an agent for inhibiting the activity of miR-134 to the individual, wherein the agent is delivered to the brain of the individual.

7. The method of claim 6, wherein the brain-related disorder characterized by development of seizures is a brain injury likely to precipitate epilepsy.

8. The method of claim 7, wherein the brain injury likely to precipitate epilepsy is selected from the group consisting of stroke, hypoxia, infection, tumor, a neurodegenerative disorder, and a metabolic and autoimmune disorder that causes seizures.

9. The method of claim 8, wherein the brain injury is caused by stroke.

10. The method of claim 8, wherein the metabolic disorder that causes seizures is hypoglycaemia, glycogen storage disease, pyruvate dehydrogenase deficiency, acquired hypoparathyroidism, or Adenylosuccinate lyase (ADSL) deficiency.

11. The method of claim 8, wherein the autoimmune disorder that causes seizures is multiple sclerosis, diabetes mellitus, or systemic lupus erythematosus.

12. The method of claim 8, wherein the agent that inhibits the activity of miR-134 is a specific low molecular weight inhibitor of miR-134 expression selected from an anti-sense molecule, a siRNA molecule, a shRNA molecule, a micro-RNA sponge, and a decoy oligonucleotide.

13. The method of claim 12, wherein the anti-sense molecule is an antagomir or a tiny seed target LNA oligonucleotide.

14. The method of claim 13, wherein the agent is a miR-134 antagomir.

15. The method of claim 14, wherein the anti-sense molecule has a sequence selected from SEQ ID NO: 5 or SEQ ID NO: 7.

* * * * *

SEQUENCE LISTING

<160> NUMBER OF SEQ ID NOS: 7

<210> SEQ ID NO 1
<211> LENGTH: 22
<212> TYPE: RNA
<213> ORGANISM: Homo sapiens

<400> SEQUENCE: 1
ugugacuggu ugaccagagg gg                                              22

<210> SEQ ID NO 2
<211> LENGTH: 1273
<212> TYPE: DNA
<213> ORGANISM: Homo sapiens

<400> SEQUENCE: 2
ggaccacaat ttcaactcca gggaaggggg actgtgccag caccactcca agggaggtga     60
gtgaagggtt gcccaaactc cagtgtgttc ctaggacacc cgtaagctgc ctcactaatg    120
ctcggtgtcc actctgtcca caggatggtg gttggcagcc actcccttg gagaagtgga    180 aggggactcc ttgtctgtct tgtctctgct tttctgtggt acttgaagag aagttgttcg    240
tggtggattc gctttactta tgacgaatca ttcacggaca acactttttt cagtaccaaa    300
tgctacctct aaggacttcc tggacacaat ggcagcttca ggaaagatag tctttgtgtc    360
aaccatgtgg aaaagccaag aatggatggc gggccatgga caatgcgctg acctagctgt    420
aagtcacctg gcccgataat ccgagcctcc catgcaccta taggaggtct tcccatgggt    480
ctcaccaact ctggggaatc agctgtggtt ctgtcaccag cgtcacctca caagactttg    540
aagagaggct ccctgggccc caggccgact tccagaagag atgttggtgt cagcaccgtc    600
cagggtgtgt gactggttga ccagaggggc atgcactgtg ttcaccctgt gggccaccta    660
gtcaccaacc ctcagcatca ctcccactcc aggaagactt tccagagctc ccaccaactc    720
tggggaagcg gccatggact tgctgtgact gcttggtgga ctgcgatgac acgtgctctt    780
gggggtgtat gtttacttaa aatgcaatga gtcagccttg gcagcccctt caccactgtg    840
acagcctcct tgaagtgttg acttccgatg tgggacgcca tgttgtcttc tgttgaggga    900
cctgatgtgg gccagctttt ctcctgggtg tgtgactgaa tccttcttcc cagagcatgt    960
gctgcctttg ttaggtctgt cacgtcgtcc tctaataccc agcatcctgt ctctccctag   1020
gaggctccat ggagataatg cggctttggg aagcggccat gattctcctg tcagggacca   1080
gtgagctacg caaaagctcc ctgtcttgtc tggaaggacg aactgcatcc ttgctgctgg   1140
ggagaaggca gtgccctcag cactcccttta aggtaagtgc gcctcgggtg agcatgcact   1200
taatgtgggt gtatgtcact cggctcggcc cactacccaa tactatccca cccattccta   1260
acaggactcc cga                                                      1273

<210> SEQ ID NO 3
<211> LENGTH: 73
<212> TYPE: DNA
<213> ORGANISM: Homo sapiens

<400> SEQUENCE: 3
cagggtgtgt gactggttga ccagaggggc atgcactgtg ttcaccctgt gggccaccta     60
gtcaccaacc ctc                                                       73

<210> SEQ ID NO 4
<211> LENGTH: 15

```
<212> TYPE: DNA
<213> ORGANISM: Artificial Sequence
<220> FEATURE:
<223> OTHER INFORMATION: Scrambled antagomir; LNA- and 3'-cholesterol
      modified oligonucleotides

<400> SEQUENCE: 4
cgtctagcca cctag                                                      15

<210> SEQ ID NO 5
<211> LENGTH: 19
<212> TYPE: DNA
<213> ORGANISM: Artificial Sequence
<220> FEATURE:
<223> OTHER INFORMATION: mir-134 antagomir; LNA- and 3'-cholesterol
      modified oligonucleotides

<400> SEQUENCE: 5
cctctggtca accagtcac                                                  19

<210> SEQ ID NO 6
<211> LENGTH: 31
<212> TYPE: RNA
<213> ORGANISM: Homo sapiens

<400> SEQUENCE: 6
ucucucccuc uggucaacca gucacaaggc u                                    31

<210> SEQ ID NO 7
<211> LENGTH: 22
<212> TYPE: DNA
<213> ORGANISM: Artificial Sequence
<220> FEATURE:
<223> OTHER INFORMATION: oligonucleotide

<400> SEQUENCE: 7
cccctctggt caaccagtca ca                                              22
```